United States Patent
Karathanasis et al.

(10) Patent No.: US 11,260,127 B2
(45) Date of Patent: Mar. 1, 2022

(54) MESOPOROUS SILICA NANOPARTICLES FOR DIAGNOSTIC AND THERAPEUTIC APPLICATIONS

(71) Applicant: CASE WESTERN RESERVE UNIVERSITY, Cleveland, OH (US)

(72) Inventors: Efstathios Karathanasis, Solon, OH (US); Watuthentrige Pubudu M. Peiris, Twinsburg, OH (US); Vindya Perera, Hudson, OH (US); Lisa Bauer, Sandusky, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 16/163,211

(22) Filed: Oct. 17, 2018

(65) Prior Publication Data

US 2019/0111133 A1   Apr. 18, 2019

Related U.S. Application Data

(60) Provisional application No. 62/573,303, filed on Oct. 17, 2017.

(51) Int. Cl.
| | | |
|---|---|---|
| *A61K 41/00* | (2020.01) | |
| *A61K 9/51* | (2006.01) | |
| *A61K 47/69* | (2017.01) | |
| *A61P 35/00* | (2006.01) | |
| *A61P 35/04* | (2006.01) | |
| *A61K 31/704* | (2006.01) | |
| *A61K 31/495* | (2006.01) | |
| *A61K 31/7068* | (2006.01) | |
| *A61K 31/519* | (2006.01) | |
| *A61K 9/00* | (2006.01) | |

(52) U.S. Cl.
CPC ........ *A61K 41/0028* (2013.01); *A61K 9/0009* (2013.01); *A61K 9/0019* (2013.01); *A61K 9/5115* (2013.01); *A61K 31/495* (2013.01); *A61K 31/519* (2013.01); *A61K 31/704* (2013.01); *A61K 31/7068* (2013.01); *A61K 47/6923* (2017.08); *A61K 47/6929* (2017.08); *A61P 35/00* (2018.01); *A61P 35/04* (2018.01)

(58) Field of Classification Search
CPC .................. A61K 41/0028; A61K 47/6923
See application file for complete search history.

(56) References Cited

U.S. PATENT DOCUMENTS

| | | | |
|---|---|---|---|
| 9,439,966 B2 | 9/2016 | Karathanasis et al. | |
| 2010/0303716 A1* | 12/2010 | Jin | A61M 37/0092 424/1.11 |
| 2011/0130616 A1* | 6/2011 | Seeney | A61K 9/1676 600/14 |

OTHER PUBLICATIONS

Lu et al., Chem Commun, 2013, 49, 11436-11438.*
Peiris, et al., "Treatment of Invasive Brain Tumors Using a Chain-like Nanoparticle", Cancer Res; 75(7) Apr. 1, 2015.
Rauwerdink et al., "Concurrent quantification of multiple nanoparticle bound states", Med. Phys. 38 „3 . . . , Mar. 2011.
Simoes, et al., "On the formulation of pH-sensitive liposomes with long circulation times", Advanced Drug Delivery Reviews, vol. 56, Issue 7, Apr. 23, 2004, pp. 947-965.
La, et al., "Thermosensitive liposomes entrapping iron oxide nanoparticles for controllable drug release", Nanotechnology. Apr. 1, 2009;20(13).
Agarwal, et al. "Remote triggered release of doxorubicin in tumors by synergistic application of thermosensitive liposomes and gold nanorods", ACS Nano. Jun. 28, 2011;5(6).
Brazel, et al., "Magnetothermally-responsive nanomaterials: combining magnetic nanostructures and thermally-sensitive polymers for triggered drug release", Pharm Res. Mar. 2009;26(3).
Lee, et al., "Exchange-coupled magnetic nanoparticles for efficient heat induction", Nat Nanotechnol. Jun. 26, 2011;6(7).
Peiris et al., "Enhanced Delivery of Chemotherapy to Tumors Using a Multi-Component Nanochain with Radiofrequency-Tunable Drug Release", ACS Nano. May 22, 2012; 6(5).

* cited by examiner

*Primary Examiner* — Kyle A Purdy
(74) *Attorney, Agent, or Firm* — Tarolli, Sundheim, Covell & Tummino LLP

(57) ABSTRACT

A system for delivering a therapeutic agent to cell or tissue of a subject includes a mesoporous silica iron oxide nanoparticle with one or more therapeutic agents that are contained in a mesoporous silica layer of the nanoparticle and a remote radiofrequency (RF) energy source for applying RF energy to the nanoparticle effective to release the one or more therapeutic agents from the nanoparticle by mechanical tumbling and/or vibration of the nanoparticle, wherein release of the one or more therapeutic agents not caused by a hyperthermic response of the nanoparticle to the RF energy.

20 Claims, 10 Drawing Sheets

MESOPOROUS SILICA NANOPARTICLES FOR DIAGNOSTIC AND THERAPEUTIC APPLICATIONS

RELATED APPLICATION

This application claims priority from U.S. Provisional Application No. 62/573,303, filed Oct. 17, 2017, the subject matter of which is incorporated herein by reference in its entirety.

GOVERNMENT FUNDING

This invention was made with government support under Grant Nos. RU01CA198892 and R01CA177716, awarded by The National Institutes of Health (NIH) and the National Cancer Institute (NCI). The United States government has certain rights in the invention.

TECHNICAL FIELD

This application relates to mesoporous silica nanoparticles and to the use of the nanoparticles for diagnostic and therapeutic applications.

BACKGROUND

Nanoparticles can be used as delivery vehicles for therapeutic and imaging agents with improved biodistribution and increased delivery efficiency to solid tumors. In particular, nanomedicine's greatest advantage over conventional therapies is its ability to combine more than one function by enabling the design of multifunctional nanoparticles that target, image, and destroy tumors. This has led to the development of various nanoparticle delivery systems, such as liposomes, dendrimers, other lipidic and polymeric nanoparticles, and metal nanoparticles (e.g., iron oxide and gold).

Various triggered release mechanisms have been applied in the design of nanoparticle systems to address the drug delivery limitations to tumors. Such systems include temperature or pH sensitive liposomes or polymeric nanoparticles. However, the release mechanism of these particles relies on changes in environmental factors (e.g., pH, temperature), which may be non-uniform throughout the tumor volume. There remains a need for nanoparticles having a rapid cargo release mechanism that is not based on environmental factors that allows for the highly tolerable targeted delivery of multiple doses of therapeutic and/or imaging agents.

SUMMARY

Embodiments described herein relate to iron mesoporous silica nanoparticles (FeMSNs) for use in diagnostic and therapeutic applications. The FeMSNs include an iron core, such as an iron oxide core, and an outer layer or shell of mesoporous silica, which can be coated on or over the iron core. The nanoparticles can optionally include one or more therapeutic or imaging agents that can be loaded on or within the mesoporous silica layer and can be controllably released from the mesoporous silica layer by stimulation of the FeMSNs with radiofrequency (RF) energy from a remote source.

The FeMSNs can be used in a system for delivering a therapeutic agent to a cell or tissue of a subject. The system can include the FeMSNs and a remote RF energy source for applying RF energy to the nanoparticle effective to release the one or more therapeutic agents from the mesoporous silica layer of the nanoparticle by mechanical tumbling and/or vibration of the nanoparticle. The release of the one or more therapeutic agents is not caused by a hyperthermic response of the nanoparticle to the RF energy and/or the RF energy effective to release the one or more therapeutic agents is less than that required to induce a localized temperature increase in the subject.

In some embodiments, the FeMSNs can have an average or nominal diameter of about 50 nm to about 150 nm, and the iron oxide core can have an average or nominal diameter of about 10 nm to about 50 nm.

The therapeutic agent can include, for example, an anti-cancer agent or anti-proliferative agent. The FeMSNs can also include one or more targeting moieties. The targeting moieties can be linked to surfaces of the FeMSNs. The spacing and location of the targeting moieties on the FeMSNs can be controlled to facilitate delivery, targeting, and/or therapeutic efficacy of the nanoparticles when administered to a subject.

In some embodiments the RF energy is applied at a frequency of about 1 kHz to about 50 kHz, for example, about 1 kHz to about 20 kHz.

Other embodiments relate to a method of treating cancer in a subject. The method can include administering to the subject a plurality of FeMSNs that include an iron oxide core and layer of mesoporous silica coated over the core. The FeMSNs can include or be linked to an anti-cancer agent or anti-proliferative agent. Radiofrequency (RF) energy can be applied to the administered nanoparticles from a remote source external to the subject effective to release the one or more therapeutic agents from the mesoporous silica layer of the nanoparticles by mechanical tumbling and/or vibration of the nanoparticles. The release of the one or more therapeutic agents is not caused by a hyperthermic response of the nanoparticle to the RF energy and/or the RF energy effective to release the one or more therapeutic agents is less than that required to induce a localized temperature increase in the subject.

DETAILED DESCRIPTION

Figure 1:
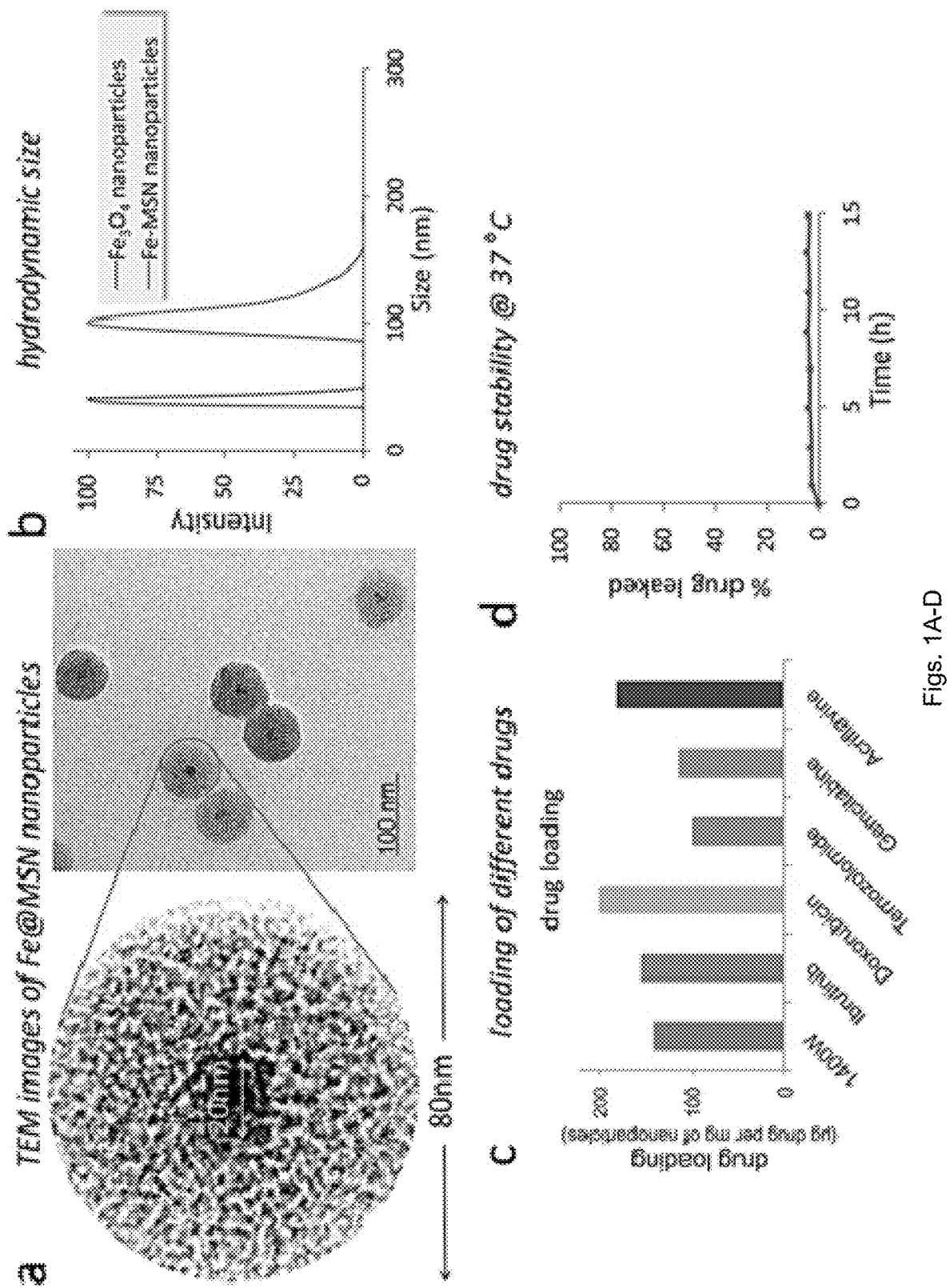
FIGS. 1(A-D) illustrate (A) Schematic of the Fe@MSN nanoparticles. (B) TEM image of the @MSN nanoparticle. (C) Size distribution of the starting iron oxide core and the final Fe@MSN nanoparticle obtained by DLS. (D) Different drugs were loaded into the Fe@MSN nanoparticles including a chemotherapeutic drug (doxorubicin or DOX), an iNOS inhibitor (1400 W) and a BMX inhibitor (Ibrutinib).

All scientific and technical terms used in this application have meanings commonly used in the art unless otherwise specified. The definitions provided herein are to facilitate understanding of certain terms used frequently herein and are not meant to limit the scope of the application.

The articles "a" and "an" are used herein to refer to one or to more than one (i.e., to at least one) of the grammatical object of the article. By way of example, "an element" means one element or more than one element.

As used herein, the term "sample" can refer to a specimen or culture obtained from any source, as well as clinical, research, biological and environmental samples. Biological samples may be obtained from animals (including humans) and encompass cells, fluids, solids, tissues, and organs, and whole organisms.

As used herein, the term "subject" can refer to any animal including, but not limited to, humans and non-human animals (e.g., rodents, arthropods, insects, fish (e.g., zebrafish)), non-human primates, ovines, bovines, ruminants, lagomorphs, porcines, caprines, equines, or canines felines, ayes, etc.).

As used herein, the terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

As used herein, the terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

As used herein, the term "polynucleotide" can refer to oligonucleotides, nucleotides, or to a fragment of any of these, to DNA or RNA (e.g., mRNA, rRNA, tRNA) of genomic or synthetic origin, which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids, i.e., oligonucleotides, containing known analogues of natural nucleotides. The term can also encompass nucleic acid-like structures with synthetic backbones.

As used herein, the term "polypeptide" can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term can also include peptides and polypeptide fragments, motifs and the like, glycosylated polypeptides, and all "mimetic" and "peptidomimetic" polypeptide forms.

As used herein, the term "small molecule" can refer to lipids, carbohydrates, polynucleotides, polypeptides, or any other organic or inorganic molecules.

As used herein, the term "imaging agent" can refer to a biological or chemical moiety that may be used to detect, image, and/or monitor the presence and/or progression of a cell cycle, cell function/physiology, condition, pathological disorder and/or disease.

As used herein, the terms "treating" or "treatment" of a disease can refer to executing a treatment protocol to eradicate at least one diseased cell. Thus, "treating" or "treatment" does not require complete eradication of diseased cells.

As used herein, the term "targeting moiety" can refer to a molecule or molecules that are able to bind to and complex with a biomarker. The term can also refer to a functional group that serves to target or direct a nanoparticle, therapeutic agent or anti-cancer agent to a particular location, cell type, diseased tissue, or association. In general, a "targeting moiety" can be directed against a biomarker.

As used herein, the term "molecular signature" can refer to a unique expression pattern of one or more biomarkers (e.g., gene(s) or protein(s)) of a cell.

As used herein, the term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In exemplary embodiments, antibodies used with the methods and compositions described herein are derivatives of the IgG class.

As used herein, the term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 10 amino acids and more typically will comprise at least about 200 amino acids.

As used herein, the term "diabodies" refers to dimeric scFvs. The components of diabodies typically have shorter peptide linkers than most scFvs and they show a preference for associating as dimers.

As used herein, the term "epitope" refers to a physical structure on a molecule that interacts with a selective component. In exemplary embodiments, epitope refers to a desired region on a target molecule that specifically interacts with a selectivity component.

As used herein, the term "Fab" refers to an antibody fragment that is essentially equivalent to that obtained by reduction of the disulfide bridge or bridges joining the two heavy chain pieces in the F(ab')$_2$ fragment. Such fragments may be enzymatically or chemically produced by fragmentation of an intact antibody, recombinantly produced from a gene encoding the partial antibody sequence, or it may be wholly or partially synthetically produced.

As used herein, the term "F(ab')$_2$" refers to an antibody fragment that is essentially equivalent to a fragment obtained by digestion of an immunoglobulin (typically IgG) with the enzyme pepsin at pH 4.0-4.5. Such fragments may be enzymatically or chemically produced by fragmentation of an intact antibody, recombinantly produced from a gene encoding the partial antibody sequence, or it may be wholly or partially synthetically produced.

As used herein, the term "Fv" refers to an antibody fragment that consists of one $V_H$ and one $V_L$ domain held together by noncovalent interactions. The term "dsFv" is used herein to refer to an Fv with an engineered intermolecular disulfide bond to stabilize the $V_H$-$V_L$ pair.

As used herein, the term "immunogen" traditionally refers to compounds that are used to elicit an immune response in an animal, and is used as such herein. However, many techniques used to produce a desired selectivity component, such as the phage display and aptamer methods described below, do not rely wholly, or even in part, on animal immunizations. Nevertheless, these methods use compounds containing an "epitope," as defined above, to select for and clonally expand a population of selectivity components specific to the "epitope." These in vitro methods mimic the selection and clonal expansion of immune cells in vivo, and, therefore, the compounds containing the "epitope" that is used to clonally expand a desired population of phage, aptamers and the like in vitro are embraced within the definition of "immunogens."

As used herein, the terms "single-chain Fvs" and "scFvs" refers to recombinant antibody fragments consisting of only the variable light chain ($V_L$) and variable heavy chain ($V_H$) covalently connected to one another by a polypeptide linker. Either $V_L$ or $V_H$ may be the NH$_2$-terminal domain. The polypeptide linker may be of variable length and composition so long as the two variable domains are bridged without serious steric interference. In exemplary embodiments, the linkers are comprised primarily of stretches of glycine and serine residues with some glutamic acid or lysine residues interspersed for solubility.

An "effective amount" can refer to that amount of nanoparticles including one or more therapeutic agents, or to the amount of therapeutic agents themselves, that results in amelioration of symptoms or a prolongation of survival in the subject and relieves, to some extent, one or more symptoms of the disease or returns to normal (either partially or completely) one or more physiological or biochemical parameters associated with or causative of the disease. Therapeutic agents can include any agent (e.g., molecule, drug, pharmaceutical composition, etc.) capable of preventing, inhibiting, or arresting the symptoms and/or progression of a disease.

This application relates to iron mesoporous silica nanoparticles (FeMSNs) that include an inner iron core, such as an iron oxide core, and an outer layer or shell of mesoporous silica, which can be coated around the core, and to the use of the FeMSNs in diagnostic and therapeutic applications. The layer of mesoporous silica protects the iron core from aggregation and provides support for surface modification of the FeMSNs with functional groups. The pores of the mesopourous silica layer can allow small molecules to diffuse into the outer silica layer of the FeMSNs. This process, in turn, advantageously allows for highly stable loading of therapeutic and imaging agents with negligible leakage as well as the release/liberation of the therapeutic agent from the FeMSNs in response to an externally applied energy source, such as radiofrequency (RF) signal.

The FeMSNs described herein can be used in diagnostic and/or therapeutic applications to deliver therapeutic agents and/or imaging agents to cells and/or tissue of a subject as well as actively target cells and/or tissue of a subject upon systemic administration (e.g., intravenous, intravascular, intraarterial infusion) to the subject. The FeMSNs can interact with vessel walls to, for example, target vascular specific biomarkers or extravasate through leaky tumor endothelium in tumor interstitium. The FeMSNs can also be remotely activated with a remote energy source to selectively release therapeutic agents and/or imaging agents to targeted cells and/or tissue of the subject.

Use of the term "mesoporous silica" does not preclude materials other than mesoporous silica from also being incorporated within the silica layer. In some embodiments, the layer of mesoporous silica may be substantially spherical with a plurality of pore openings through the surface providing access to the pores. However, the layer of mesoporous silica can have shapes other than substantially spherical shapes in other embodiments of the current invention. Generally, the layer of mesoporous silica defines an outer surface between the pore openings, as well as side walls within the pores. The pores can extend through the layer of mesoporous silica to another pore opening, or can extend only partially through the layer of mesoporous silica such that it has a bottom surface of the pore defined by the layer of mesoporous silica.

The FeMSNs may be uniform (e.g., being about the same size) or of variable size. In general, the FeMSNs can have dimensions small enough to allow the nanoparticles to be systemically administered to a subject and targeted to cells and tissue of the subject. In some embodiments, the nanoparticles can have a size that facilitates extravasation of the FeMSNs in cancer therapy or diagnosis. Typically, the FeMSNs can have a longest straight dimension (e.g., diameter) of about 150 nm or less. In some embodiments, the FeMSNs can have an average diameter of about 100 nm or less. Smaller nanoparticles, e.g., having average diameters of about 75 nm or less are used in some embodiments. Typically, the iron oxide core of the FeMSNs can have an average diameter of about 10 nm to about 50 nm. In a particular embodiment, the FeMSNs can have an average diameter of about 100 nm with an iron oxide core having a diameter of about 40 nm. In another embodiment, the FeMSNs can have an average diameter of about 100 nm with an iron oxide core having a diameter of about 30 nm. In yet another embodiment, the FeMSNs can have an average diameter of about 75 nm with an iron oxide core having a diameter of about 18 nm.

The FeMSNs can be prepared by first using a coprecipitation method to synthesize the iron oxide cores. The silica layer can be added to the iron oxide core using a base-catalyzed sol-gel process enhanced by the surfactant cetyltrimethylammonium bromide (CTAB) to produce highly ordered mesoporous silica layer. Additionally, various functional groups can be introduced onto the silica surface using well known methods in order to conjugate the nanoparticles with other molecules or substrates.

In some embodiments, the FeMSNs can additionally or optionally include at least one targeting moiety that is capable of targeting and/or adhering the FeMSN to a cell or tissue of interest. The targeting moiety can comprise any molecule, or complex of molecules, which is/are capable of interacting with an intracellular, cell surface, or extracellular biomarker of the cell. The biomarker can include, for example, a cellular protease, a kinase, a protein, a cell surface receptor, a lipid, and/or fatty acid. Other examples of biomarkers that the targeting moiety can interact with include molecules associated with a particular disease. For example, the biomarkers can include cell surface receptors implicated in cancer development, such as epidermal growth factor receptor and transferrin receptor, or cancer metastasis, such as $\alpha_v\beta_3$ integrin. The targeting moieties can interact with the biomarkers through, for example, non-covalent binding, covalent binding, hydrogen binding, van der Waals forces, ionic bonds, hydrophobic interactions, electrostatic interaction, and/or combinations thereof.

The targeting moieties can include, but are not limited to, synthetic compounds, natural compounds or products, macromolecular entities, bioengineered molecules (e.g., polypeptides, lipids, polynucleotides, antibodies, antibody fragments), and small entities (e.g., small molecules, neurotransmitters, substrates, ligands, hormones and elemental compounds).

In one example, the targeting moiety can include an antibody, such as a monoclonal antibody, a polyclonal antibody, or a humanized antibody. The antibody can include Fv fragments, single chain Fv (scFv) fragments, Fab' fragments, F(ab')2 fragments, single domain antibodies, camelized antibodies and other antibody fragments. The antibody can also include multivalent versions of the foregoing antibodies or fragments thereof including monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

Preparation of antibodies can be accomplished by any number of methods for generating antibodies. These methods typically include the step of immunization of animals, such as mice or rabbits, with a desired immunogen (e.g., a desired target molecule or fragment thereof). Once the mammals have been immunized, and boosted one or more times with the desired immunogen(s), antibody-producing hybridomas may be prepared and screened according to well known methods. See, for example, Kuby, Janis, Immunology, Third Edition, pp. 131-139, W.H. Freeman & Co. (1997), for a general overview of monoclonal antibody production, that portion of which is incorporated herein by reference.

In vitro methods that combine antibody recognition and phage display techniques can also be used to allow one to amplify and select antibodies with very specific binding capabilities. See, for example, Holt, L. J. et al., "The Use of Recombinant Antibodies in Proteomics," Current Opinion in Biotechnology, 2000, 11:445-449, incorporated herein by reference. These methods typically are much less cumbersome than preparation of hybridomas by traditional monoclonal antibody preparation methods.

In some embodiments, phage display technology may be used to generate a targeting moiety specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding a scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as a Fab' fragment, may be cloned into phage display vectors for surface expression on phage particles. The phage may be any phage, such as lambda, but typically is a filamentous phage, such as Fd and M13, typically M13.

In phage display vectors, the $V_H$-linker-$V_L$ sequence is cloned into a phage surface protein (for M13, the surface proteins g3p (pIII) or g8p, most typically g3p). Phage display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacterial cells is the Recombinant Phage Antibody System (RPAS), commercially available from Amersham Pharmacia Biotech, Inc. of Piscataway, N.J. and the pSKAN Phagemid Display System, commercially available from MoBiTec, LLC of Marco Island, Fla. Phage display systems, their construction, and screening methods are described in detail in, among others, U.S. Pat. Nos. 5,702,892, 5,750,373, 5,821,047 and 6,127,132, each of which is incorporated herein by reference in their entirety.

The targeting moiety need not originate from a biological source. The targeting moiety may, for example, be screened from a combinatorial library of synthetic peptides. One such method is described in U.S. Pat. No. 5,948,635, incorporated herein by reference, which described the production of phagemid libraries having random amino acid insertions in the pIII gene of M13. These phage may be clonally amplified by affinity selection as described above.

The immunogens used to prepare targeting moieties having a desired specificity will generally be the target molecule, or a fragment or derivative thereof. Such immunogens may be isolated from a source where they are naturally occurring or may be synthesized using methods known in the art. For example, peptide chains may be synthesized by 1-ethyl-3-[dimethylaminoproply]carbodiimide (EDC)-catalyzed condensation of amine and carboxyl groups. In certain embodiments, the immunogen may be linked to a carrier bead or protein. For example, the carrier may be a functionalized bead such as SASRIN resin commercially available from Bachem, King of Prussia, Pa. or a protein such as keyhole limpet hemocyanin (KLH) or bovine serum albumin (BSA). The immunogen may be attached directly to the carrier or may be associated with the carrier via a linker, such as a non-immunogenic synthetic linker (for example, a polyethylene glycol (PEG) residue, amino caproic acid or derivatives thereof) or a random, or semi-random polypeptide.

In certain embodiments, it may be desirable to mutate the binding region of the polypeptide targeting moiety and select for a targeting moiety with superior binding characteristics as compared to the un-mutated targeting moiety. This may be accomplished by any standard mutagenesis technique, such as by PCR with Taq polymerase under conditions that cause errors. In such a case, the PCR primers could be used to amplify scFv-encoding sequences of phagemid plasmids under conditions that would cause mutations. The PCR product may then be cloned into a phagemid vector and screened for the desired specificity, as described above.

In other embodiments, the targeting moieties may be modified to make them more resistant to cleavage by proteases. For example, the stability of targeting moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of targeting moiety may be of the D configuration. The switch from L to D amino acids neutralizes the digestion capabilities of many of the ubiquitous peptidases found in the digestive tract. Alternatively, enhanced stability of a targeting moiety comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of a targeting moiety may be achieved by intercalating one or more dextrorotatory amino acids (such as, dextrorotatory phenylalanine or dextrorotatory tryptophan) between the amino acids of targeting moiety. In exemplary embodiments, such modifications increase the protease resistance of a targeting moiety without affecting the activity or specificity of the interaction with a desired target molecule.

In certain embodiments, a targeting moiety as described herein may comprise a homing peptide, which selectively directs the nanoparticle to a targeted cell. Homing peptides for a targeted cell can be identified using various methods well known in the art. Many laboratories have identified the homing peptides that are selective for cells of the vasculature of brain, kidney, lung, skin, pancreas, intestine, uterus, adrenal gland, retina, muscle, prostate, or tumors. See, for example, Samoylova et al., 1999, Muscle Nerve, 22:460; Pasqualini et al., 1996 Nature, 380:364; Koivunen et al., 1995, Biotechnology, 13:265; Pasqualini et al., 1995, J. Cell Biol., 130:1189; Pasqualini et al., 1996, Mole. Psych., 1:421, 423; Rajotte et al., 1998, J. Clin. Invest., 102:430; Rajotte et al., 1999, J. Biol. Chem., 274:11593. See, also, U.S. Pat. Nos. 5,622,6999; 6,068,829; 6,174,687; 6,180,084; 6,232,287; 6,296,832; 6,303,573; and 6,306,365.

Phage display technology provides a means for expressing a diverse population of random or selectively randomized peptides. Various methods of phage display and methods for producing diverse populations of peptides are well known in the art. For example, methods for preparing diverse populations of binding domains on the surface of a phage have been described in U.S. Pat. No. 5,223,409. In particular, phage vectors useful for producing a phage display library as well as methods for selecting potential binding domains and producing randomly or selectively mutated binding domains are also provided in U.S. Pat. No. 5,223,409. Similarly, methods of producing phage peptide display libraries, including vectors and methods of diversifying the population of peptides that are expressed, are also described in Smith et al., 1993, Meth. Enzymol., 217:228-257, Scott et al., Science, 249:386-390, and two PCT publications WO 91/07141 and WO 91/07149. Phage display technology can be particularly powerful when used, for example, with a codon based mutagenesis method, which can be used to produce random peptides or randomly or desirably biased peptides (see, e.g., U.S. Pat. No. 5,264,563). These or other well-known methods can be used to produce a phage display library, which can be subjected to the in vivo phage display method in order to identify a peptide that homes to one or a few selected tissues.

In vitro screening of phage libraries has previously been used to identify peptides that bind to antibodies or cell surface receptors (see, e.g., Smith, et al., 1993, Meth. Enzymol., 217:228-257). For example, in vitro screening of phage peptide display libraries has been used to identify novel peptides that specifically bind to integrin adhesion receptors (see, e.g., Koivunen et al., 1994, J. Cell Biol. 124:373-380), and to the human urokinase receptor (Goodson, et al., 1994, Proc. Natl. Acad. Sci., USA 91:7129-7133).

In certain embodiments, the targeting moiety may comprise a receptor molecule, including, for example, receptors, which naturally recognize a specific desired molecule of a target cell. Such receptor molecules include receptors that have been modified to increase their specificity of interaction with a target molecule, receptors that have been modified to interact with a desired target molecule not naturally recognized by the receptor, and fragments of such receptors (see, e.g., Skerra, 2000, J. Molecular Recognition, 13:167-187). A preferred receptor is a chemokine receptor. Exemplary chemokine receptors have been described in, for example, Lapidot et al, 2002, Exp Hematol, 30:973-81 and Onuffer et al, 2002, Trends Pharmacol Sci, 23:459-67.

In some embodiments, the targeting moiety can include cyclo (ARG-GLY-ASP-D-Phe-Cys) or (cRGDfC), which is a ligand for vascular targeting and metastasis. In some embodiments, a detergent compatible can be used to quantify the number of peptides per FeMSN particles. In one particular embodiment, each FeMSN nanoparticle includes about 3000 c(RGDfC) targeting ligands.

In other embodiments, the targeting moiety can be targeting peptide comprising an EGF peptide. The EGF peptide may comprise the amino acid sequence YHWYGYTPQNVI-amide. The peptide may be synthesized by any method known in the art. For example, the EGF peptide may be synthesized manually using Fmoc protected amino acids (Peptides International, Louisville, Ky.) on rink-amide CLEAR resin (Peptides International, Louisville, Ky., 100-200 mesh size, 0.4 milliequivalents/gram).

In still other embodiments, the targeting moiety may comprise a ligand molecule, including, for example, ligands which naturally recognize a specific desired receptor of a target cell, such as a Transferrin (Tf) ligand. Such ligand molecules include ligands that have been modified to increase their specificity of interaction with a target receptor, ligands that have been modified to interact with a desired receptor not naturally recognized by the ligand, and fragments of such ligands.

In other embodiments, the targeting moiety may comprise an aptamer. Aptamers are oligonucleotides that are selected to bind specifically to a desired molecular structure of the target cell. Aptamers typically are the products of an affinity selection process similar to the affinity selection of phage display (also known as in vitro molecular evolution). The process involves performing several tandem iterations of affinity separation, e.g., using a solid support to which the diseased immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids (PNAs) and phosphorothioate nucleic acids.

In yet other embodiments, the targeting moiety may be a peptidomimetic. By employing, for example, scanning mutagenesis to map the amino acid residues of a protein, which is involved in binding other proteins, peptidomimetic compounds can be generated which mimic those residues which facilitate the interaction. Such mimetics may then be used as a targeting moiety to deliver the composition to a target cell. For instance, non-hydrolyzable peptide analogs of such resides can be generated using benzodiazepine (e.g., see Freidinger et al. in Peptides: Chemisty and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al., 1986, J Med Chem 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., 1985, Tetrahedron Lett 26:647; and Sato et al., 1986, J Chem Soc Perkin Trans 1:1231), and β-aminoalcohols (Gordon et al., 1985, Biochem Biophys Res Cummun 126:419; and Dann et al., 1986, Biochem Biophys Res Commun 134:71).

The targeting moiety may be attached directly to the FeMSN nanoparticle. In an exemplary embodiment, a targeting moiety may be conjugated onto an amine-functionalized FeMSN nanoparticle via maleimide chemistry. In some embodiments, the targeting moiety may be associated with or coupled to the nanoparticles using a linker. The linker can be of any suitable length and contain any suitable number of atoms and/or subunits. The linker can include one or combination of chemical and/or biological moieties. Examples of chemical moieties can include alkyl groups, methylene carbon chains, ether, polyether, alkyl amide linkers, alkenyl chains, alkynyl chains, disulfide groups, and polymers, such as poly(ethylene glycol) (PEG), functionalized PEG, PEG-chelant polymers, dendritic polymers, and combinations thereof. Examples of biological moieties can include peptides, modified peptides, streptavidin-biotin or avidin-biotin, polyaminoacids (e.g., polylysine), polysaccharides, glycosaminoglycans, oligonucleotides, phospholipid derivatives, and combinations thereof.

In some embodiments, the FeMSN nanoparticles can include multiple types of targeting moieties and the spacing and location of the targeting moieties on each nanoparticle can be controlled to facilitate delivery, targeting, and/or therapeutic efficacy of the nanoparticle cargo.

In other embodiments, the FeMSN nanoparticles can include imaging agents (or detectable moieties) and/or therapeutic agents that are contained in, or conjugated to, the mesoporous silica layer of the nanoparticles. Therapeutic agents contained in, and/or linked to the nanoparticles can include any substance capable of exerting a biological or therapeutic effect in vitro and/or in vivo. Therapeutic agents can also include any therapeutic or prophylactic agent used in the treatment (including the prevention, diagnosis, alleviation, or cure) of a malady, affliction, condition, disease or injury in a subject. Non-limiting examples of therapeutic agents include, but are not limited to anti-cancer agents, anti-proliferative agents, chemotherapeutic agents, anti-neurodegenerative agents, and anti-cardiovascular disease agents. The therapeutic agents can be in the form of biologically active ligands, small molecules, peptides, polypeptides, proteins, DNA fragments, DNA plasmids, interfering RNA molecules, such as siRNAs, oligonucleotides, and DNA encoding for shRNA.

Imaging agents can include any substance that may be used for imaging or detecting a region of interest (ROI) in a subject and/or diagnosing the presence or absence of a disease or diseased tissue in a subject. The imaging agent can be selected such that it generates a signal, which can be measured and whose intensity is related (preferably proportional) to the distribution of the imaging agent and nanoparticle in the subject. Examples of imaging agents include, but are not limited to: radionuclides, fluorescent dyes, chemiluminescent agents, MRI contrast agents, enzymatic moieties, colorimetric labels, and magnetic labels. In one example, the imaging agent can include a radiolabel that is detected using gamma imaging wherein emitted gamma irradiation of the appropriate wavelength is detected. Methods of gamma imaging include, but are not limited to, SPECT and PET. For SPECT detection, the chosen radiolabel can lack a particular emission, but will produce a large number of photons in, for example, a 140-200 keV range.

In another example, the imaging can an include MRS/MRI radiolabel, such as gadolinium, iron, $^{19}F$, $^{13}C$, that is coupled (e.g., attached or complexed) with the nanoparticle using general organic chemistry techniques. The imaging agent can also include radiolabels, such as $^{18}F$, $^{19}F$, $^{11}C$, $^{15}O$, $^{75}Br$, or $^{76}Br$ for PET by techniques well known in the art and are described by Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, NY 1986) the contents of which are hereby incorporated by reference. The imaging can also include $^{123}I$ for SPECT.

The imaging agent can further include known metal radiolabels, such as Technetium-99m (99mTc), $^{111}In$, $^{3}H$, $^{14}C$, $^{35}S$, $^{125}I$, $^{121}I$, and $^{112}In$. Preparing radiolabeled derivatives of Tc99m is well known in the art for use in single photon emission tomography. See, for example, Zhuang et al., "Neutral and stereospecific Tc-99m complexes: [99mTc] N-benzyl-3,4-di-(N-2-mercaptoethyl)-amino-pyrrolidines (P-BAT)" Nuclear Medicine & Biology 26(2):217-24, (1999); Oya et al., "Small and neutral Tc(v)O BAT, bisaminoethanethiol (N2S2) complexes for developing new brain imaging agents" Nuclear Medicine & Biology 25(2):135-40, (1998); and Hom et al., "Technetium-99m-labeled receptor-specific small-molecule radiopharmaceuticals: recent developments and encouraging results" Nuclear Medicine & Biology 24(6):485-98, (1997).

Thus, a label is any composition detectable by spectroscopic, photochemical, biochemical, immunochemical, electrical, optical or chemical means. Useful labels in the present invention include magnetic beads (e.g. Dynabeads™), a triarylmethane dye (e.g., crystal violet), fluorescent dyes (e.g., fluorescein isothiocyanate, cyanines such as Cy5, Cy5.5 and analogs thereof (e.g., sulfo-Cyanine 5 NHS ester and Cy5.5 maleimide), Alexa Fluor dye (e.g., Alexa Fluor 647 and AlexaFluor 555), DyLight 649, Texas red, rhodamine B, and the like), other imaging agents such as microbubbles (for ultrasound imaging), enzymes (e.g., horse radish peroxidase, alkaline phosphatase and others commonly used in an ELISA), and calorimetric labels such as colloidal gold or colored glass or plastic (e.g. polystyrene, polypropylene, latex, and the like) beads. See also Handbook of Fluorescent Probes and Research Chemicals, $6^{th}$ Ed., Molecular Probes, Inc., Eugene Oreg., which is incorporated herein by reference.

In some embodiments, the therapeutic agent can be an anti-cancer agent or anti-proliferative agent that is contained in, and/or linked to the FeMSN nanoparticles. In an exemplary embodiment, a therapeutic agent is loaded into phosphonate functionalized FeMSN nanoparticles. The phrase "anti-cancer agent" or "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms. There are a large number of anti-proliferative agent agents available in commercial use, in clinical evaluation and in pre-clinical development, which can be loaded into, and administered in association with, the FeMSN nanoparticles.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

Examples of antimetabolite antineoplastic agents include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine phosphate, N-(2'-furanidyl)-5-fluorouracil, Daiichi Seiyaku FO-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin, all of which are disclosed in U.S. Pat. No. 6,916,800, which is herein incorporated by reference in its entirety.

Examples of alkylating-type anti-proliferative agents include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr) 2, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol.

Examples of antibiotic-type anti-proliferative agents that may be used in the present invention include, but are not limited to Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

Examples of hormonal-type anti-proliferative agents that may be used in the present invention include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598; BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; episteride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

Miscellaneous antineoplastic agents include, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel, Encore Pharmaceuticals E7869, ellipsrabin, elliptinium acetate, Tsumura EPMTC, ergotamine, etoposide, etretinate, EULEXIN, Cell Pathways EXISULIND (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, seienium(selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

In particular embodiments, the anti-neoplastic agent can one or more of a chemotherapeutic drug (e.g., doxorubicin, gemcitabine, temozolomide), and a small molecule inhibitor (e.g., 1400 W (iNOS inhibitor) and Ibrutinib (BMX inhibitor)).

In some embodiments, the therapeutic agent can be an anti-neurodegenerative agent that is contained in, and/or linked to the FeMSN nanoparticles. Anti-neurodegenerative agents can include any agents used in the treatment of neurodegenerative diseases such as, but not limited to, diseases and disorders in which the myelin which surrounds the neuron is either absent, incomplete, not formed properly, or is deteriorating. Such disease include, but are not limited to, multiple sclerosis (MS), neuromyelitis optica (NMO), progressive multifocal leukoencephalopathy (PML), encephalomyelitis (EPL), central pontine myelolysis (CPM), adrenoleukodystrophy, Alexander's disease, Pelizaeus Merzbacher disease (PMD), Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, acute disseminated encephalitis, Guillian-Barre syndrome, Marie-Charcot-Tooth disease and Bell's palsy.

Examples of anti-neurodegenerative disease agents can include, but are not limited to L-dopa, cholinesterase inhibitors, anticholinergics, dopamine agonists, steroids, and immunomodulators such as interferon beta-la and beta-lb (Avonex and Betaseron respectively), natalizumab (Copaxone) natalizumab (Tysabri), glatiramer acetate (Copaxone) or mitoxantrone.

In some embodiments, the therapeutic agent can be an anti-cardiovascular disease agent that is contained in, and/or linked to the FeMSN nanoparticles. Anti-cardiovascular disease agents include, but are not limited to, beta blockers, anti-hypertensives, cardiotonics, anti-thrombotics, vasodilators, hormone antagonists, inotropes, diuretics, endothelin antagonists, calcium channel blockers, phosphodiesterase inhibitors, ACE inhibitors, angiotensin type 2 antagonists and cytokine blockers/inhibitors, and HDAC inhibitors.

In some embodiments, the anti-cardiovascular disease agent can include an antihyperlipoproteinemic agent, an antiarteriosclerotic agent, an antithrombotic/fibrino lytic agent, a blood coagulant, an antiarrhythmic agent, an anti-hypertensive agent, a vasopressor, a treatment agent for congestive heart failure, an antianginal agent, an antibacterial agent or a combination thereof.

An antihyperlipoproteinemic agent can include, but is not limited to, aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof, acifran, azacosterol, benfluorex, β-benzalbutyramide, carnitine, chondroitin sulfate, clomestrone, detaxtran, dextran sulfate sodium, eritadenine, furazabol, meglutol, melinamide, mytatrienediol, ornithine, γ-oryzanol, pantethine, pentaerythritol tetraacetate, a-phenylbutyramide, pirozadil, probucol (lorelco), β-sitosterol, sultosilic acid-piperazine salt, tiadenol, triparanol and xenbucin.

The anti-cardiovascular disease agent can include an antiarteriosclerotic agent such as pyridinol carbamate. An anti-cardiovascular disease agent can include an antithrombotic/fibrinolytic agent including, but not limited to anticoagulants (acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin); anticoagulant antagonists, antiplatelet agents (aspirin, a dextran, dipyridamole (persantin), heparin, sulfinpyranone (anturane) and ticlopidine (ticlid)); thrombolytic agents (tissue plaminogen activator (activase), plasmin, pro-urokinase, urokinase (abbokinase) streptokinase (streptase), anistreplase/APSAC (eminase)); thrombolytic agent antagonists or combinations thereof). Anti-cardiovascular disease agents may also include an blood coagulant including, but not limited to, thrombolytic agent antagonists (amiocaproic acid (amicar) and tranexamic acid (amstat); antithrombotics (anagrelide, argatroban, cilstazol, daltroban, defibrotide, enoxaparin, fraxiparine, indobufen, lamoparan, ozagrel, picotamide, plafibride tedelparin, ticlopidine and triflusal); and anticoagulant antagonists (protamine and vitamine K1).

An anti-cardiovascular disease agent can also include an antiarrhythmic agent including, but not limited to, Class I antiarrythmic agents (sodium channel blockers), Class II antiarrythmic agents (beta-adrenergic blockers), Class II antiarrythmic agents (repolarization prolonging drugs), Class IV antiarrhythmic agents (calcium channel blockers) and miscellaneous antiarrythmic agents. Non-limiting examples of sodium channel blockers include Class IA (disppyramide (norpace), procainamide (pronestyl) and quinidine (quinidex)); Class IB (lidocaine (xylocaine), tocainide (tonocard) and mexiletine (mexitil)); and Class IC antiarrhythmic agents, (encamide (enkaid) and fiecamide (tambocor)).

Non-limiting examples of a beta blocker (also known as a β-adrenergic blocker, a β-adrenergic antagonist or a Class II antiarrythmic agent) include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfmalol, talinolol, tertatolol, timolol, toliprolol and xibinolol. In certain aspects, the beta Mocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol. Non-limiting examples of an agent that prolongs repolarization, also known as a Class III antiarrhythmic agent, include amiodarone (cordarone) and sotalol (betapace).

Non-limiting examples of a calcium channel blocker, otherwise known as a Class IV antiarrhythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexyline. In certain embodiments a calcium channel blocker comprises a long-acting dihydropyridine (nifedipine-type) calcium antagonist.

Non-limiting examples of miscellaneous antiarrhymic agents include adenosine (adenocard), digoxin (lanoxin), acecainide, ajmaline, amoproxan, aprindine, bretylium tosylate, bunaftine, butobendine, capobenic acid, cifenline, disopyranide, hydroquinidine, indecainide, ipatropium bromide, lidocaine, lorajmine, lorcamide, meobentine, moricizine, pirmenol, prajmaline, propafenone, pyrinoline, quinidine polygalcaturonate, quinidine sulfate and viquidil.

An anti-cardiovascular disease agent can also include an antihypertensive agent including, but not limited to, alphaibeta blockers (labetalol (normodyne, trandate)), alpha blockers, anti-angiotensin II agents, sympatholytics, beta blockers, calcium channel blockers, vasodilators and miscellaneous antihypertensives.

Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

Non-limiting examples of anti-angiotension II agents include angiotensin converting enzyme inhibitors and angiotension II receptor antagonists. Non-limiting examples of angiotensin converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan. Non-limiting examples of a sympatholytic include a centrally acting sympatholytic or a peripherally acting sympatholytic. Non-limiting examples of a centrally acting sympatholytic, also known as a central nervous system (CNS) sympatholytic, include clonidine (catapres), guanabenz (wytens guanfacine (tenex) and methyldopa (aldomet). Non-limiting examples of a peripherally acting sympatholytic include a ganglion blocking agent, an adrenergic neuron blocking agent, a β-adrenergic blocking agent or an α1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

In certain embodiments, an antihypertensive agent may comprise a vasodilator (e.g., a cerebral vasodilator, a coronary vasodilator or a peripheral vasodilator). In particular embodiments, a vasodilator comprises a coronary vasodilator including, but not limited to, amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(P-diethylaminoethyl ether), hexobendine, itramin tosylate, mannitol hexanitrane, rnedibazine, nicorglycerin, pentaerythritol tetranitrate, pentrinitrol, perhexyline, pimethylline, trapidil, tricromyl, trimetazidine, trolnitrate phosphate and visnadine.

A vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyriclyl ketone thiosemicarbazone, muzolimine, pargyline, pempidine, pinacidil, piperoxan, pnmaperone, a protoveratrine, raubasine, rescimetol, rilmenidene, saralasin, sodium nitrorusside, ticrynafen, trimethaphan camsylate, tyrosinase and urapidil. In certain aspects, an antihypertensive may comprise an arylethanolamine derivative (amosulalol, bufuralol, dilevalol, labetalol, pronethalol, sotalol and sulfmalol); a benzothiadiazine derivative (althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide); a N-carboxyalkyl(peptide/lactam) derivative (alacepril, captopril, cilazapril, delapril, enalapril, enalaprilat, fosinopril, lisinopril, moveltipril, perindopril, quinapril and ramipril); a dihydropyridine derivative (amlodipine, felodipine, isradipine, nicardipine, nifedipine, nilvadipine, nisoldipine and nitrendipine); a guanidine derivative (bethanidine, debrisoquine guanabenz, guanacline, guanadrel, guanazodine, guanethidine, guanfacine, guanochlor, guanoxabenz and guanoxan); a hydrazines/phthalazine (budralazine, cadralazine, dihydralazine, endralazine, hydracarbazine, hydralazine, pheniprazine, pildralazine and todralazine); an imidazole derivative (clonidine, lofexidine, phentolamine, tiamenidine and tolonidine); a quanternary ammonium compound (azamethonium bromide, chlorisondamine chloride, hexamethonium, pentacynium bis(methylsulfate), pentamethonium bromide, pentolinium tartrate, phenactropinium chloride and trimethidinium methosulfate); a reserpine derivative (bictaserpine, deserpidine, rescinnamine, reserpine and syrosingopine); or a sulfonamide derivative (ambuside, clopamide, farosemide, indapamide, quinethazone, tripamide and xipamide).

Anti-cardiovascular disease agents can include a vasopressor. Vasopressors generally are used to increase blood pressure during shock, which may occur during a surgical procedure. Non-limiting examples of a vasopressor, also known as an antihypotensive include amezinium methyl sulfate, angiotensin amide, dimetofrine, dopamine, etifelmin, etilefrin, gepefrine, metaraminol, midodrine, norepinephrine, pholedrine and synephrine.

In some embodiments, an anti-cardiovascular disease agent can include treatment agents for congestive heart failure including, but not limited to, anti-angiotension II agents, afterload-preload reduction treatment (hydralazine (apresoline) and isosorbide dinitrate (isordil, sorbitrate)), diuretics, and inotropic agents.

Non-limiting examples of a diuretic include a thiazide or benzothiadiazine derivative (e.g., althiazide, bendroflumethazide, beizthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furterene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, triparnide, xipamide), a uracil (e.g., aminometradine, arnisornetradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea.

Non-limiting examples of a positive inotropic agent, also known as a cardiotonic, include acefylline, an acetyldigitoxin, 2-amino-4-picoline, aminone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In some embodiments, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include aminone (inocor).

Additional therapeutic agents that can be contained in, and/or linked to the FeMSN nanoparticles include anti-inflammatory, anti-viral, anti-fungal, anti-mycobacterial, antibiotic, amoebicidal, trichomonocidal, analgesic, anti-microbial and/or steroid drugs. In some embodiments, one or more therapeutic agents contained in, and/or linked to the FeMSN nanoparticles can include β-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (e.g., for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), didanosine (dideoxyinosine, ddl, Videx™), stavudine (d4T, Zerit™), zalcitabine (dideoxycytosine, ddC, Hivid™), nevirapine (Viramune™), lamivudine (Epivir™, 3TC), pro tease inhibitors, saquinavir (Invirase™, Fortovase™), ritonavir (Norvir™), nelfmavir (Viracept™), efavirenz (Sustiva™), abacavir (Ziagent™), amprenavir (Agenerase™) indinavir (Crixivan™), ganciclovir, AzDU, delavirdine (Kescriptor™), kaletra, trizivir, rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparagyinase and combinations foregoing.

In other embodiments, one or more therapeutic agents contained in, and/or linked to the FeMSN nanoparticles can include immunomodulatory agents, anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steroids, non-steriodal antiinflammatory drugs (e.g., aspirin, ibuprofen, diclofenac, and COX-2 inhibitors), and leukotreine antagonists (e.g., montelukast, methyl xanthines, zafirlukast, and zileuton), β2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), other anti-viral agents, and antibiotics (e.g., dactinomycin (formerly actinomycin), bleomycin, erythomycin, penicillin, mithramycin, and anthramycin (AMC)).

Advantageously, the FeMSN nanoparticles described here allow for loading large amounts of therapeutic agent cargo onto and/or within the mesoporous silica layer of the FeMSN nanoparticle. In addition, the FeMSN nanoparticles allow for the loading of two or more drugs having differing physiochemical properties. In an exemplary embodiment, the FeMSN nanoparticles can be loaded with a combination of a chemotherapeutic drug (doxorubicin), an iNOS inhibitor (1400 W) and a BMX inhibitor (Ibrutinib) (see FIG. 2B). The amounts or type of therapeutic agent loaded onto and/or within the mesoporous silica layer of the FeMSN nanoparticle can be controlled by changing altering physical parameters of the nanoparticles. For example, the surface charge or pH of the FeMSN nanoparticles can be modified to alter drug release kinetics or cargo load compositions.

Release of the therapeutic agent or imaging agent from the nanoparticle can be remotely triggered by a remote energy source that supplies energy to the FeMSN nanoparticle effective to release the therapeutic agent or imaging agent from the mesoporous silica pores of the nanoparticle. For example, the iron oxide core of the nanoparticles can be responsive to energy, from a remote source that is effective to release a therapeutic or imaging agent from the mesoporous silica layer of the nanoparticle after administering the FeMSN to a subject.

The remote source can be external or remote from a subject, which allows non-invasive remote release of the therapeutic agent to the subject. Advantageously, a nanoparticle that allows remote release of the therapeutic agent, such as a chemotherapeutic agent (e.g., doxorubicin) can target or be targeted to specific cells or tissue of subject, such as tumors, cancers, and metastases, by systemic administration (e.g., intravenous, intravascular, or intraarterial infusion) to the subject and once targeted to the cells or tissue remotely released to specifically treat the targeted cells or tissue of subject (e.g., tumors, cancers, and metastasis). Targeting and selective release of the chemotherapeutic agents to malignant cancer metastases allows treatment of such metastases using chemotherapeutics, which would provide an otherwise neglible effect if not targeted and remotely released using the nanoparticles described herein.

In some embodiments, mild radiofrequency (RF) energy from a remote RF energy source can be used to release a therapeutic agent or imaging agent from the mesoporous silica layer of the FeMSN nanoparticle. The mesoporous silica layer of the FeMSN nanoparticle can have a plurality of pore opening through the surface providing access to pores that have been loaded with and contain a therapeutic agent or imaging agent. The iron oxide core of the nanoparticles can be responsive to RF energy from a remote RF energy source and act as a mechanic transducer to mechanically tumble, vibrate, resonate, and/or oscillate upon application of RF energy from the energy source. Application of mild (low) RF energy from RF source can rapidly release/liberate the therapeutic agent or imaging agent from the mesoporous silica layer of the nanoparticle due to tumbling, vibration, and/or oscillation of the iron oxide of the nanoparticle core in response to an externally applied radiofrequency (RF) signal. When magnetic iron oxide core nanoparticles are subjected to an external electromagnetic field, it must overcome thermal and viscous forces to achieve magnetic reversal and align with the applied field. In its effort to align with the alternating RF field, the nanoparticles described herein tumble, oscillate, and/or vibrate according to their governing magnetic relaxation mechanisms, providing kinetic energy to the 'entrapped' therapeutic or imaging molecules in the pores of the nanoparticles' silica component. This added kinetic energy enables cargo agents to be liberated from the nanoparticles.

In some embodiments, the RF energy applied can be a low frequency or RF energy. The low frequency of about 1 kHz to about 50 kHz, for example about 1 kHz to about 20 kHz. RF fields can be produced using any suitable device capable of producing low-power RF frequencies. Exemplary devices include an audio amplifier and electromagnets. In some embodiments, a coil or antenna can be used to deliver the RF energy in order to control RF field decay away from the RF source. It will be appreciated that other remote energy sources can be used to release the therapeutic agent or imaging agent from the FeMSN nanoparticles and that the selection of the energy source will depend at least in part on the physical parameters of the nanoparticles and the desired electromagnetic field. Because the cargo release mechanism is dependent on the magnetic relaxation response of the magnetic FeMSN nanoparticles, altering physical parameters of the nanoparticle described above and/or the electromagnetic field, may alter drug release kinetics. In some embodiments, the drug release rate can be modulated by adjusting the operating parameters (e.g., frequency) of the RF source (e.g., 1 or 10 kHZ frequency).

The mild RF energy applied to the nanoparticles can be that amount effective cause the metal nano-particles to mechanically tumble, vibrate, resonate, and/or oscillate at an amount or level effective to release the therapeutic agent from pores of the nanoparticle mesoporous silica layer without causing a hyperthermic response and/or substantial heating (e.g., greater than 1° C., 2° C., 3° C., or 5° C.) around the nanoparticle when administered to a subject. Alternatively, the remote energy source can be, for example, a minimally invasive laser that can be inserted in vivo in the subject being treated or positioned external or ex vivo the subject. The energy from laser can be in the near infrared range to allow deep radiation penetration into tissue and remote release of therapeutic agent or imaging agent.

In an exemplary embodiment, upon administration of a plurality of FeMSN nanoparticles to a subject by, for example, intravascular administration, the nanoparticles can target the tumor, cancer, or metastases being treated. The nanoparticle can be imaged by, for example, magnetic resonance imaging or computed tomography, to confirm localization and targeting of the nanoparticle to the tumor or cancer cells. The nanoparticle targeted to the tumor, cancer, or metastases can be applied mild RF energy from a remote RF energy that is external to the subject being treated to mechanically resonate or oscillate the iron oxide core FeMSN nanoparticle and rapidly release the therapeutic agent from the mesoporous silica layer of the nanoparticles.

In some embodiments, the FeMSN nanoparticles described herein can be formulated in a pharmaceutical composition. Formulation of pharmaceutical composition for use in the modes of administration noted below (and others) are described, for example, in *Remington's Pharmaceutical Sciences* (18$^{th}$ edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

For example, pharmaceutical compositions can contain can be in the form of a sterile aqueous solution containing, if desired, additional ingredients, for example, preservatives, buffers, tonicity agents, antioxidants, stabilizers, nonionic wetting or clarifying agents, and viscosity increasing agents.

Examples of preservatives for use in such a solution include benzalkonium chloride, benzethonium chloride, chlorobutanol, thimerosal and the like. Examples of buffers include boric acid, sodium and potassium bicarbonate, sodium and potassium borates, sodium and potassium carbonate, sodium acetate, and sodium biphosphate, in amounts sufficient to maintain the pH at between about pH 6 and about pH 8, and for example, between about pH 7 and about pH 7.5. Examples of tonicity agents are dextran 40, dextran 70, dextrose, glycerin, potassium chloride, propylene glycol, and sodium chloride.

Examples of antioxidants and stabilizers include sodium bisulfite, sodium metabisulfite, sodium thiosulfite, and thiourea. Examples of wetting and clarifying agents include polysorbate 80, polysorbate 20, poloxamer 282 and tyloxapol. Examples of viscosity-increasing agents include gelatin, glycerin, hydroxyethylcellulose, hydroxmethylpropylcellulose, lanolin, methylcellulose, petrolatum, polyethylene glycol, polyvinyl alcohol, polyvinylpyrrolidone, and carboxymethylcellulose Examples of formulations for parenteral administration can include aqueous solutions of the composition in water-soluble form, for example, water-soluble salts and alkaline solutions. Especially preferred salts are maleate, fumarate, succinate, S,S tartrate, or R,R tartrate. In addition, suspensions of the composition as appropriate oily injection suspensions can be administered. Aqueous injection suspensions can contain substances that increase the viscosity of the suspension, such as sodium carboxymethyl cellulose, sorbitol and/or dextran. Optionally, the suspension may also contain stabilizers.

Formulations for topical administration to the skin include, for example, ointments, creams, gels and pastes comprising the composition in a pharmaceutical acceptable carrier. The formulation of the composition for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

In some embodiments, the FeMSN nanoparticles described herein can be used in a method for treating a disorder in a subject. The disorder can include diseased cells. The cells can include a diseased cell or healthy cell that is derived from, or a part of, various tissue types, such as neuronal tissue (including both neuron and glia), connective tissue, hepatic tissue, pancreatic tissue, kidney tissue, bone marrow tissue, cardiac tissue, retinal tissue, intestinal tissue, lung tissue, endothelium tissue, cartilage, skeletal muscle, cardiac muscle, other cardiac tissue that is not muscle, smooth muscle, bone, tendon, ligament, adipose tissue and skin. Depending upon the particular application, the cell may be in vivo or ex vivo. Ex vivo cells can be collected as part of one or more samples using one or a combination of known techniques (e.g., biopsy) and, if needed, further processed (e.g., centrifuged) prior to culture, analysis, etc.

In certain embodiments, the FeMSN nanoparticles described herein can be used in a method for treating a neoplastic, neurodegenerative, or cardiovascular disease or disorder in a subject. In some embodiments, the FeMSN nanoparticles described herein can be used in a method for treating cancer in a subject.

In some embodiments, a therapeutically effective amount of the FeMSN nanoparticles can be administered in vivo to a subject to treat the subject. The FeMSN nanoparticles may be administered by any convenient route, such as by infusion or bolus injection or by absorption through epithelial or mucocutaneous linings (e.g., oral mucosa, vaginal, rectal and intestinal mucosa, etc.), and may be administered together with other biologically active agents. For example, the FeMSN nanoparticles may be introduced into the central nervous system by any suitable route, including intraventricular injection, intrathecal injection, or intraventricular injection via an intraventricular catheter that is attached to a reservoir.

The FeMSN nanoparticles can also be delivered systematically (e.g., intravenously), regionally, or locally (e.g., intra- or peri-tumoral injection) by, for example, intraarterial, intratumoral, intravenous, parenteral, intrapneural cavity, topical, oral or local administration, as well as subcutaneous, intra-zacheral (e.g., by aerosol), or transmucosal (e.g., voccal, bladder, vaginal, uterine, rectal, nasal, mucosal). If delivery of the FeMSN nanoparticles to the brain is desired, the targeted nanoparticles can be injected into an artery of the carotid system of arteries (e.g., occipital artery, auricular artery, temporal artery, cerebral artery, maxillary artery etc.). As discussed above, the FeMSN nanoparticles can be formulated as a pharmaceutical composition for in vivo administration.

The FeMSN nanoparticles can be administered to the subject at an amount effective to provide a desired result(s) and to avoid undesirable physiological results. The precise dose to be employed can also depend on the route of administration, and should be decided according to the judgment of a medical practitioner and each subject's circumstances. In addition, known in vitro and in vivo assays may optionally be employed to help identify optimal dosage ranges. Effective doses may be extrapolated from dose-response curves derived from in vitro or in vivo test systems.

The FeMSN nanoparticles can be administered in a variety of unit dosage forms, depending upon the particular cell or tissue being treated, the general medical condition of each subject, the method of administration, and the like. Details on dosages are well described in the scientific literature. The exact amount and concentration of the targeted FeMSN nanoparticles, or the "effective dose", can be routinely determined (e.g., by a medical practitioner). The "dosing regimen" will depend upon a variety of factors, such as whether the cell or tissue to be treated is disseminated or local, the general state of the subject's health, the subject's age, and the like. Using guidelines describing alternative dosing regimens, e.g., from the use of other agents and compositions, the skilled artisan can readily determine by routine trials the optimal effective concentrations of the composition.

In some embodiments, the FeMSN nanoparticles described herein can be used with in vivo imaging methods where detection and imaging of cells or tissue cannot readily be performed with traditional optical detection or imaging techniques. These methods can include, for example, endovascular detection, cancer and metastasis imaging, infection or inflammation imaging, imaging of cell and tissue apoptosis, localization of neurologic pathways involved in chronic pain, and localization of epilepsy foci. It will be appreciated that the FeMSN nanoparticles can be used in other in vivo methods as well as intraoperative procedures.

In each method, a plurality of the FeMSN nanoparticles can be delivered to the cells or tissue of the subject in vivo by administering an effective amount or concentration of the FeMSN nanoparticles to the subject. By effective amount or concentration of the FeMSN nanoparticles, it is meant an amount of the FeMSN nanoparticles that are effective for detecting and imaging the target cells or tissue. As apparent to one skilled in the art, such an amount will vary depending on factors that include the amount of tissue to be imaged, the rate of contact of the FeMSN nanoparticles with the tissue, any abnormalities of the tissue that may affect the efficiency of the FeMSN nanoparticles contacting or binding to the tissue.

In some embodiments, the FeMSN nanoparticles can be administered to the subject by venous (or arterial) infusion. In venous infusion, an effective amount or concentration of the FeMSN nanoparticles administered to subject can be that amount or concentration that is detectable in the tissue or cells after sequestration of the FeMSN nanoparticles in the liver, spleen, and lymph nodes. Optionally, the FeMSN nanoparticles can be administered to the subject by directly injecting the nanoparticles into cells or tissue of the area being identified or an area proximate or peripheral to the area being identified. Direct injection of the FeMSN nanoparticles can be performed by using, for example, a syringe.

In other embodiments, the nanoparticles can be administered to a subject for imaging at least one region of interest (ROI) of the subject. The ROI can include a particular area or portion of the subject and, in some instances, two or more areas or portions throughout the entire subject. The ROI can include, for example, pulmonary regions, gastrointestinal regions, cardiovascular regions (including myocardial tissue), renal regions, as well as other bodily regions, tissues, lymphocytes, receptors, organs and the like, including the vasculature and circulatory system, and as well as diseased tissue, including neoplastic or cancerous tissue (e.g., tumor tissue). The ROI can include regions to be imaged for both diagnostic and therapeutic purposes. The ROI is typically internal; however, it will be appreciated that the ROI may additionally or alternatively be external.

At least one image of the ROI can be generated using an imaging modality once the nanoparticles localize to the ROI. The imaging modality can include one or combination of known imaging techniques capable of visualizing the nanoparticles. Examples of imaging modalities can include ultrasound (US), magnetic resonance imaging (MRI), nuclear magnetic resonance (NMR), computed topography (CT), electron spin resonance (ESR), nuclear medical imaging, optical imaging, and positron emission topography (PET).

In one example, the nanoparticle can be detected with MRI and/or x-ray. MRI relies upon changes in magnetic dipoles to perform detailed anatomic imaging and functional studies. The iron oxide core of nanoparticles can also make them highly visible on X-ray, monochromatic X-ray, computed tomography (CT) and ultrasound (US).

Optionally, the nanoparticles can be modified to facilitate detection and imaging with MRI and CT as well as positron emission tomography (PET). For MRI applications, gadolinium tags can be attached to the mesoporous silica layer and/or iron oxide core. For PET applications, radioactive tags can be attached to nanoparticles. For CT applications, iodide or other heavy metals can be attached to the nanoparticles to facilitate CT contrast.

It will be appreciated the nanoparticles will likely be most useful clinically when several imaging techniques or imaging followed by a medical or surgical procedure is used. In this way, the ability to use one agent for multiple imaging modalities is optimized making the nanoparticles cost-competitive with existing contrast agents.

For multimodal imaging applications, the nanoparticles can be administered to a subject and then preoperatively imaged using, for example, CT or MRI. After preoperative imaging, the nanoparitces can serve as optical beacons for use during surgery leading to more complete resections or more accurate biopsies. In surgical resection of lesions, the completeness of resection can be assessed with intra-operative ultrasound, CT, or MRI. For example, in glioma (brain tumor) surgery, the nanoparticles can be given intravenously about 24 hours prior to pre-surgical stereotactic localization MRI. The nanoparticles can be imaged on gradient echo MRI sequences as a contrast agent that localizes with the glioma.

In other embodiments, the nanoparticles can be administered to a subject to treat and/or image a neoplastic disease in subject. Neoplastic diseases treatable by the nanoparticles described herein can include disease states in which there are cells and/or tissues which proliferate abnormally. One example of a neoplastic disease is a tumor. The tumor can include a solid tumor, such as a solid carcinoma, sarcoma or lymphoma, and/or an aggregate of neoplastic cells. The tumor may be malignant or benign, and can include both cancerous and pre-cancerous cells. The neoplastic disease can also include cancer and malignant cancer metastases.

A composition comprising the FeMSN nanoparticles described herein that includes an anti-cancer agent or anti-proliferative agent can be formulated for administration (e.g., injection) to a subject diagnosed with at least one neoplastic disorder. The nanoparticles can be formulated according to a method as described above and include, for example, at least one therapeutic agent or imaging agent as well as targeting moiety to target the neoplastic cells or cancer cells.

The stability of the therapeutic agents in the mesoporous silica layer of loaded FeMSN nanoparticles allow for the administration of high doses of multiple highly cytotoxic agents to subject's in need thereof. For example, nanoparticles can be useful in the treatment of cancers that typically display cellular heterogeneity such as those cancers characterized by the presence of multiple cancerous cell populations (e.g., multiple stem cell populations).

In an exemplary embodiment, a plurality of FeMSN nanoparticles including one or more cytotoxic therapeutic agents can be administered to a subject for the treatment of glioblastoma (GBM). In some embodiments, a first cytotoxic agent included in a FeMSN nanoparticle is effective against a first GBM cancer cell subpopulation and a second cytotoxic agent is effective against a second GBM cancer cell subpopulation. For example, a duel-drug cargo loaded on a FeMSN nanoparticle of the invention can target multiple glioblastoma stem cell subpopulations through the inhibition of BMX by the first cytotoxic agent (e.g., Ibrutinib) and iNOS by a second cytotoxic agent (e.g., 1400 W). The application of an RF field can facilitate the spread of the therapeutic agents across the brain-tumore barrier (BTB) as the nanoparticles are shown to localize at the brain-tumor interface in primary and invasive GBM sites. In further embodiments, a third cytotoxic agent can be included in a FeMSN nanoparticle for the treatment of GBM. For example, a third cytotoxic agent can include a chemotherapeutic agent such as, but not limited to, doxorubicin, gemcitabine or temozolomide.

The following examples are for the purpose of illustration only and are not intended to limit the scope of the claims, which are appended hereto.

EXAMPLE 1

Fabrication of Nanoparticles
Synthesis of Fe@MSN Nanoparticles

Iron oxide cores were synthesized by the coprecipitation method. A typical synthesis procedure is as follow: 0.6757 g of $FeCl_3 \cdot 6H_2O$ and 0.2478 g of $FeCl_2 \cdot 4H_2O$ were dissolved in 5 mL of deoxygenated water. To this solution, 2.5 mL of 0.4 M HCl was added under vigorous stirring. This iron precursor solution was added to a solution of 25 mL of 0.5 M NaOH, which was preheated to 80° C. under a constant flow of argon. The reaction mixture was then stirred for another 15 minutes at 80° C. under argon and the black precipitate was separated by using a powerful magnet. The nanoparticles were then washed several times with Milli-Q water until stable ferrofluid was obtained. To prevent the nanoparticles from agglomeration 170 mg of citric acid (in 10 mL of deionized water) was introduced and allowed to react at 80° C. for 1.5 hours. The pH of the reaction mixture was adjusted to 5.2 using concentrated ammonia solution prior to heating. The reaction was protected under argon in order to avoid any undesired side-reactions. Finally, uncoated nanoparticles and aggregates were removed by repeated centrifugation. Excess citric acid was removed by centrifugation with Amicon® Ultra-15 centrifugal filters.

The iron oxide-silica core-shell nanoparticles were prepared by using a base-catalyzed sol-gel process with a slight modification. Specifically, 50 mg of the iron oxide nanoparticles was first dispersed in 25 mL 80% ethanol by ultrasonication, to which 1 g of cetyltrimethylammonium bromide (CTAB) solution (in 5 mL of di water) was added and the resulting solution was stirred vigorously for 30 minutes. Then the mixture was heated at 60° C. for another 20 minutes to evaporate ethanol. The resulting $Fe_3O_4$/CTAB solution was added to a mixture of 45 mL of water and 0.3 mL of 2M NaOH solution and the mixture was heated up to 70° C. under stirring. Then, 0.5 mL of tetraethylorthosilicate (TEOS) was added to the reaction solution under vigorous stirring. After stirring for another 10 min, 3.3 mg of silane-PEG-NH2 was added and stirred for 24 hrs at room temperature. After that, 54 uL of Trihydroxysilylpropylmethylphosphonate was added and the solution was stirred for 4 hrs. The unreacted species were removed by washing the nanoparticles 3 times with ethanol. Finally, CTAB was extracted by refluxing the nanoparticles at 60° C. for 3 hrs with acidic ethanol (pH~1.4). Finally, aggregates were removed by repeated centrifugation.

We also show the synthesis of a ~50 mg batch size of Fe@MSN particles using starting iron oxide nanoparticles in an organic solvent. 5 mg of 10-nm oleic acid coated $Fe_3O_4$ nanoparticles were diluted in chloroform and mixed vigorously with 75 mM CTAB in $H_2O$ (550 mg CTAB in 20 mL $H_2O$). Chloroform was evaporated at 60° C. for 15 minutes to complete phase transfer of nanoparticles in $H_2O$. The suspension of nanoparticles was diluted to 160 mL with $H_2O$ and 66.5 mg NaOH was added to yield a pH near 12. The solution was heated to 70° C. before 2.734 mL TEOS and 4.83 mL EtOAc was added dropwise in succession. After 20 minutes, 100 µL of 3-(Trihydroxysilyl)propyl methyl-phosphonate OR APTES (3-Aminopropyl)triethoxysilane was added. After 2 hours, the resulting Fe@MSNs were washed twice with ethanol. The solution was resuspended in $H_2O$, and reacted with 5 mg of mPEG-silane at 70° C. for 3 hours. Remaining CTAB was removed in acidic ethanol (pH 1.35-1.55) at 60° C. for 3 hours. The final product was again washed several times in ethanol.

FIG. 1A shows a schematic illustrating the nanoparticle. TEM images of the final particle reveal that the final Fe@MSN nanoparticle exhibits a size of about 75 nm with the iron oxide being about 18 nm (FIG. 1B). In 1 mg of sample, there are $4.17 \cdot 10^{11}$ particles. Upon surface modification with silane-PEG-NH_2, Dynamic Light Scattering measurements showed that the hydrodynamic size of the starting iron oxide cores and final Fe@MSN nanoparticles was 40 and 100 nm, respectively (FIG. 1C).

We also developed a second version of the nanoparticle by changing the size of the iron oxide core. The final Fe@MSN nanoparticle exhibits a size of about 100 nm with the iron oxide being about 30 nm.

Surface Functionalization with Targeting Ligand

The cyclo (Arg-Gly-Asp-D-Phe-Cys) or c(RGDfC) was conjugated onto Fe@MSN via maleimide chemistry. First, amine-functionalized Fe@MSN in PBS were vortexed with 10 molar excess sulfo-SMCC (sulfosuccinimidyl 4-(N-maleimidomethyl)cyclohexane-1-carboxylate) for 15 minutes. Next, 5 molar excess (relative to the number of amines on Fe@MSN) of c(RGDfC) was added and allowed to react for 2 hours. The product was dialyzed against PBS using a 2000 Da MW cut-off membrane to remove unbound RGD molecules.

Bio-Rad DC protein assay was used to quantify the number of peptides per Fe@MSN particle. Briefly, 200 µL of Bio-Rad dye solution (1 part of commercially available Bio-Rad was diluted with 2 parts of distilled water and filtered through a whatman filter) was added to 800 µL of 10 mg/mL Fe@MSN and vortexed. The absorbance of the sample was obtained at 595 nm after incubating the sample for 15 minutes. The absorbance value was compared to a standard curve, which was obtained by measuring the absorbance of known concentrations of RGD with Bio-Rad dye solution.

We measured that each Fe@MSN nanoparticle was decorated with about 3000 peptides.

Loading of Drugs

DOX loading: 10 mg of phosphonate functionalized MSN nanoparticles in 2 mL of PBS were mixed with 5 mg of DOX.HCl in 1 mL water for 12 hrs. The DOX loaded nanoparticles were collected by centrifugation. The nanoparticles were washed with PBS several times to remove unbound DOX molecules.

Temozolomide loading: The pH of 10 mg of phosphonate functionalized MSN nanoparticles was ~5 by dissolving the particles in 2 mL of MES buffer. 5 mg of Temozolomide (TMZ) was added to the above nanoparticle solution and shake for 12 hrs. The TMZ-loaded nanoparticles were collected by centrifugation. The nanoparticles were washed with PBS several times to remove unbound TMZ molecules.

Gemcitabine loading: Similar to TMZ loading. 1400 W loading: The pH of 10 mg of phosphonate functionalized MSN nanoparticles (in 2 mL of PBS) was adjusted to 8.5 using a concentrated ammonia solution. 5 mg of 1400 W.2HCl in 1 mL PBS was added to the above nanoparticle solution and shake for 12 hrs. The 1400 W loaded nanoparticles were collected by centrifugation. The nanoparticles were washed with PBS several times to remove unbound 1400 W molecules.

Ibrutinib loading: 10 mg of MSN nanoparticles was first dispersed in 2 mL of DMSO. To this solution, 5 mg of Ibrutinib in 1 mL of DMSO was added and shake for 12 hrs at room temperature. The BMX loaded nanoparticles were separated by centrifugation and the nanoparticles were washed with PBS several times to remove unbound Ibrutinib molecules.

The Fe@MSN nanoparticle can be loaded with high drug cargos. Importantly, we were able to load different drugs with different physicochemical properties at comparable levels (FIG. 1D). Such drugs included chemotherapeutic agents (e.g., Doxorubicin, Gemcitabine, Temozolomide) and potent small molecule inhibitors (e.g., 1400 W, Ibrutinib). In particular, we selected inhibitors that eliminate cancer stem cell subpopulations (i.e, 1400 W is an iNOS inhibitor, Ibrutinib is a BMX inhibitor). We also evaluated the stability of the drug's incorporation in the Fe@MSN nanoparticles. In a typical leakage procedure, 1 mL of formulation was placed in dialysis tubing with 100 k MWCO and dialyzed against PBS at 37° C. Negligible leakage of drugs was observed indicating the highly stable loading of the drug cargo into the Fe@MSN particles.

RF-Triggered Drug Release

Various triggered release mechanisms have been applied in the design of nanoparticle systems to address the drug delivery limitations to tumors. Such systems include temperature or pH sensitive liposomes or polymeric nanoparticles. However, the release mechanism of these particles relies on changes in environmental factors (e.g. pH, temperature), which may be non-uniform throughout the tumor volume. In the case of Fe@MSN however, the release mechanism is not based on environmental factors. Instead, mechanical oscillations induced by an RF field trigger the release from a single Fe@MSN particle. When magnetic nanoparticles are subjected to an external magnetic field, it must overcome thermal and viscous forces to achieve magnetic reversal and align with the applied field. There are two relaxation mechanisms (Brownian and Néel relaxation) that govern this behavior. These relaxation mechanisms are dependent on several magnetic nanoparticle and environmental characteristics. Brownian relaxation is the physical rotation of a magnetically blocked core, and is dependent on hydrodynamic size of the magnetic nanoparticle (core size plus surfactant layer and any targeting agents), as well as local viscosity and temperature. This is also dependent on binding of magnetic nanoparticles—several studies have demonstrated modulation of Brownian relaxation by reversible binding to targeted receptors. Néel relaxation, a competition between magnetocrystalline energy and thermal energy, depends on the size, composition, and crystalline anisotropy of the magnetic core, as well as local temperature and applied magnetic field. In its effort to align with the alternating RF field, the Fe@MSN particle tumbles according to its governing magnetic relaxation mechanisms, providing kinetic energy to the 'entrapped' drug molecules in the pores of the nanoparticle's silica component. This added kinetic energy enables drugs to be liberated from the Fe@MSN nanoparticle. Overall, this example shows that the RF-triggered drug release mechanism is based on this mechanical tumbling or "vibration" of the particle, which is fundamentally different from heat-induced mechanism that is commonly employed by other metallic-based nanostructures. Because the drug release mechanism is dependent on the magnetic relaxation response of the magnetic nanoparticles, altering physical parameters of the nanoparticle or the magnetic field, may alter drug release kinetics. Thus, there is a wealth of opportunity for optimization and "tuning" of the Fe@MSN system.

Figure 2:
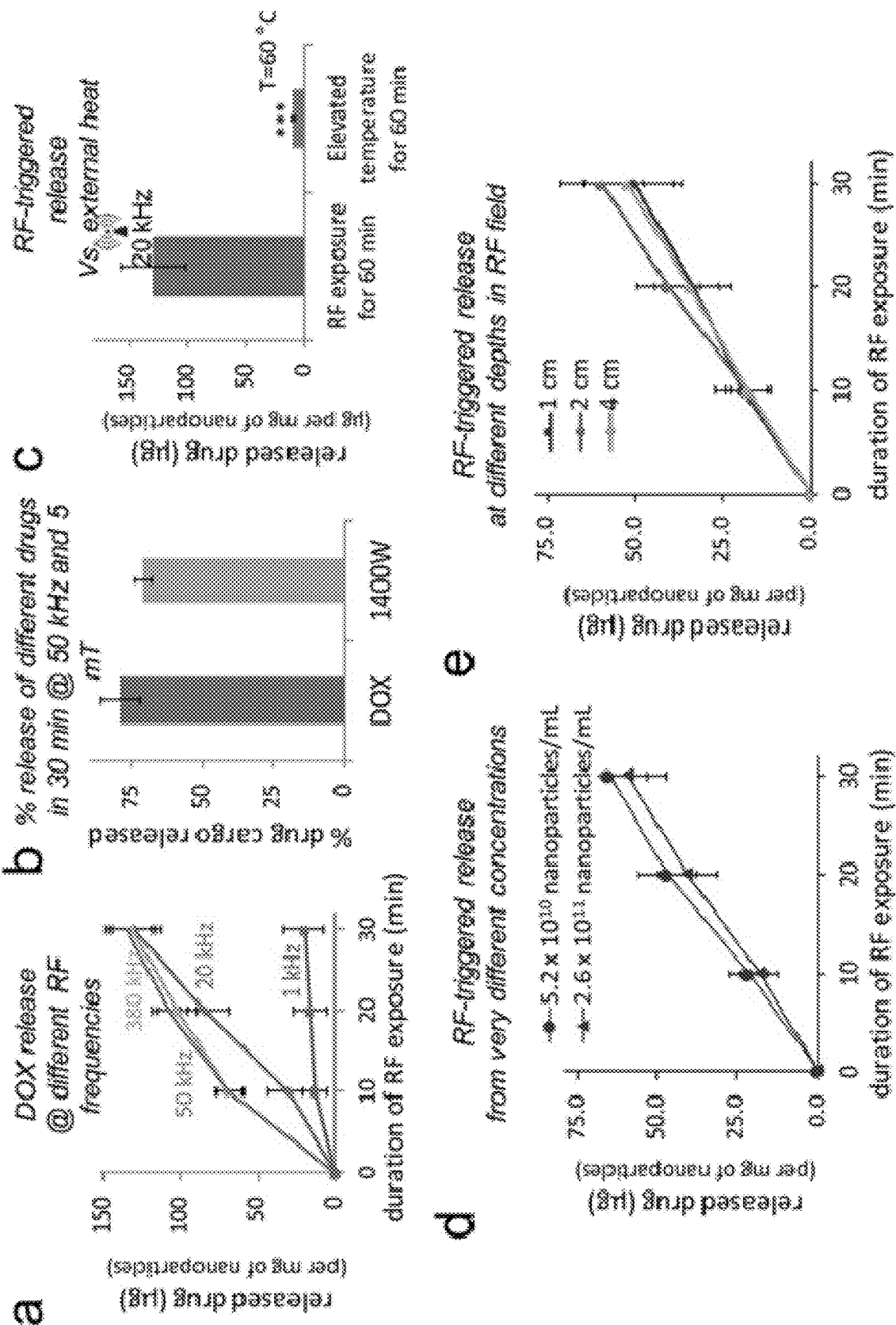
FIGS. 2(A-E) illustrate in vitro evaluation of radiofrequency (RF)-triggered drug release from Fe@MSN nanoparticles. (A) The release of DOX was triggered from Fe@MSN particles using an RF field at different frequencies (1, 20, 50 and 380 kHz; n=4). (B) The percent released drug of the nanoparticle's cargo is shown for the DOX-loaded Fe@MSN and the 1400 W-loaded Fe@MSN upon application of the RF field at 50 kHz for 30 min. (C) Effect of elevated temperature on the drug release from Fe@MSN particles with an incubation time of 60 min (n=4; unpaired t-test P<0.0001). (D) Drug release from Fe@MSN at different particle concentration under an RF field at 50 kHz. (E) Drug release from Fe@MSN particles at different depths in the RF source (RF field: 50 kHz).

The primary findings of a series of in vitro studies is summarized below:

The drug release rate of DOX can be triggered in a controlled manner under the RF field at a very low concentration of the Fe@MSN nanoparticles expected to deposit in tumor tissues during in vivo applications (FIG. 2A). Notably, the release rate could be modulated by adjusting the operating parameters of the RF field (1 or 10 kHz frequency).

No temperature increase occurred in the Fe@MSN suspension under the 'mild' RF field for the duration of a 60-min exposure. Further, when the temperature of the Fe@MSN suspension was elevated to 60° C. for 60 min by external heating, negligible drug was released (FIG. 2B). These two findings indicate that the triggered release mechanism is not based on hyperthermic effects applications, thereby minimizing the role of Neel relaxation phenomenon in RF-triggered drug release from the Fe@MSN nanoparticles.

Similar drug release rate per nanochain particle was observed from suspensions of dramatically different concentrations of Fe@MSN nanoparticles when subjected to the same RF field.

The RF-triggered drug release is nearly independent of the type of drug molecules. FIG. 2C-E show that the drug release rate of two drugs molecules (i.e., DOX and 1400 W) with very different physicochemical properties (e.g., solubility, partition coefficient) are almost identical under the same RF field.

Controlling Drug Release Rates

Figure 3:
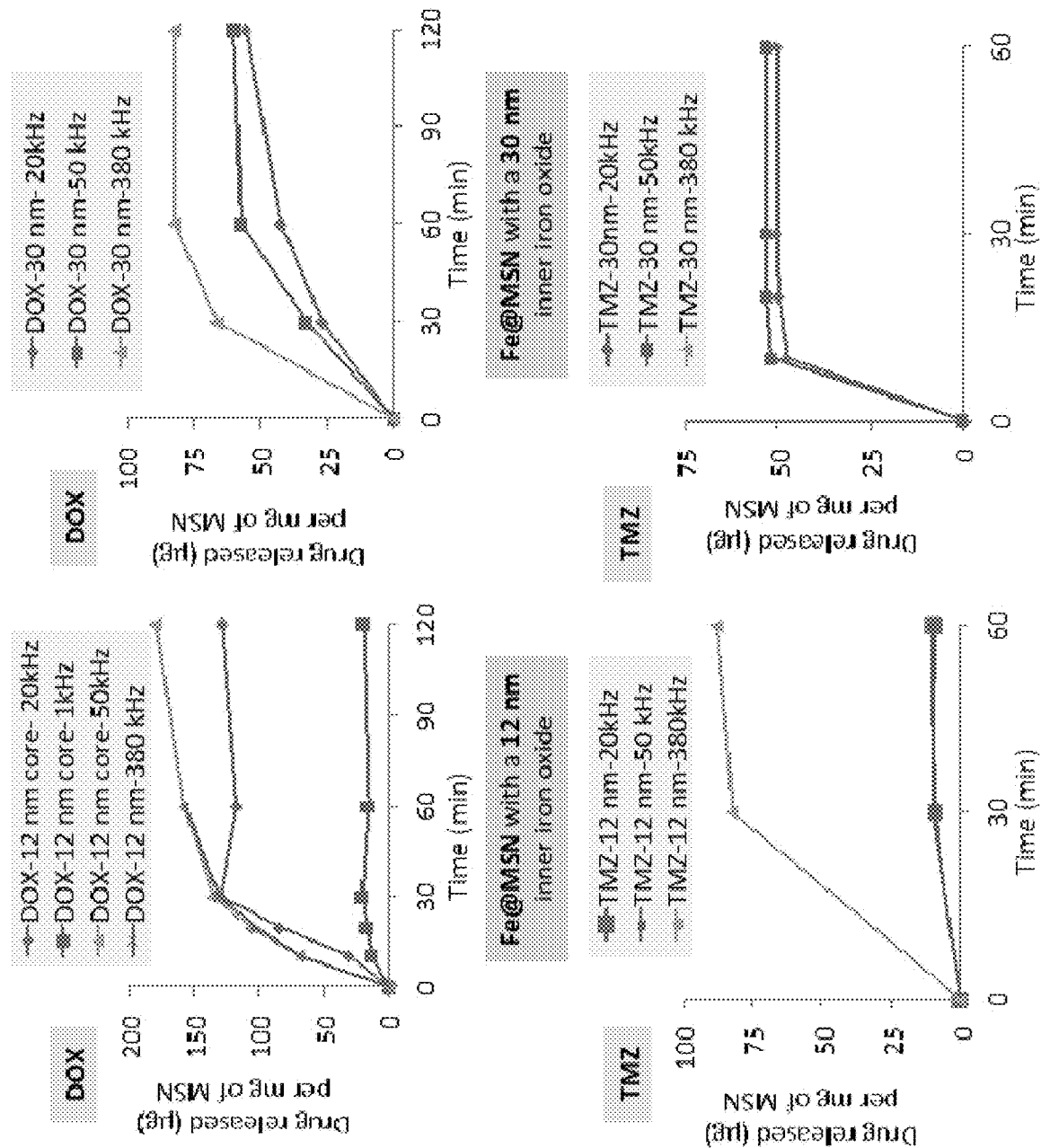
FIG. 3 illustrates plots showing the dependence of the release rate from Fe@MSN nanoparticles on the frequency of the external RF system, the size of the inner iron oxide core and the type of drug.

We compared the release rate of different drugs from Fe@MSN nanoparticles with an iron oxide core of 12 or 30 nm. FIG. 3 shows the dependence of release on the frequency of the RF.

The RF System

The RF fields required for drug release from the Fe@MSN nanoparticles are low-power (mT, 1-50 kHz), which are very safe and penetrate deep tissues with ease. Given the relatively low RF frequencies used with the nanochains compared to e.g. ultra-high field MRI (>300 MHz), the fields are well understood. Thus, the design, cost and clinical deployment of such system present a low degree of translational challenge. The components used for the current RF system are "off-the-shelf" audio power amplifiers and inexpensive 3D-printed electromagnets. Because the drug release mechanism depends on the RF field, one potential practical challenge is obtaining uniform release across a disease site, especially one at depth. This stems from the fact that the RF field decays away from the RF source. This can be controlled through the design of the coil or antenna used to deliver the RF energy, the use of coil arrays similar to those used in MRI, or the power provided to these elements. In some cases, it may be advantageous to design a coil specific to the anatomy being treated (such as a breast or head coil)—the decay of the magnetic field away from the RF source coil provides an additional degree of spatial localization and safeguards against off-target drug release.

In Vivo Applications

Organ Distribution and Targeting Studies

Figure 4:
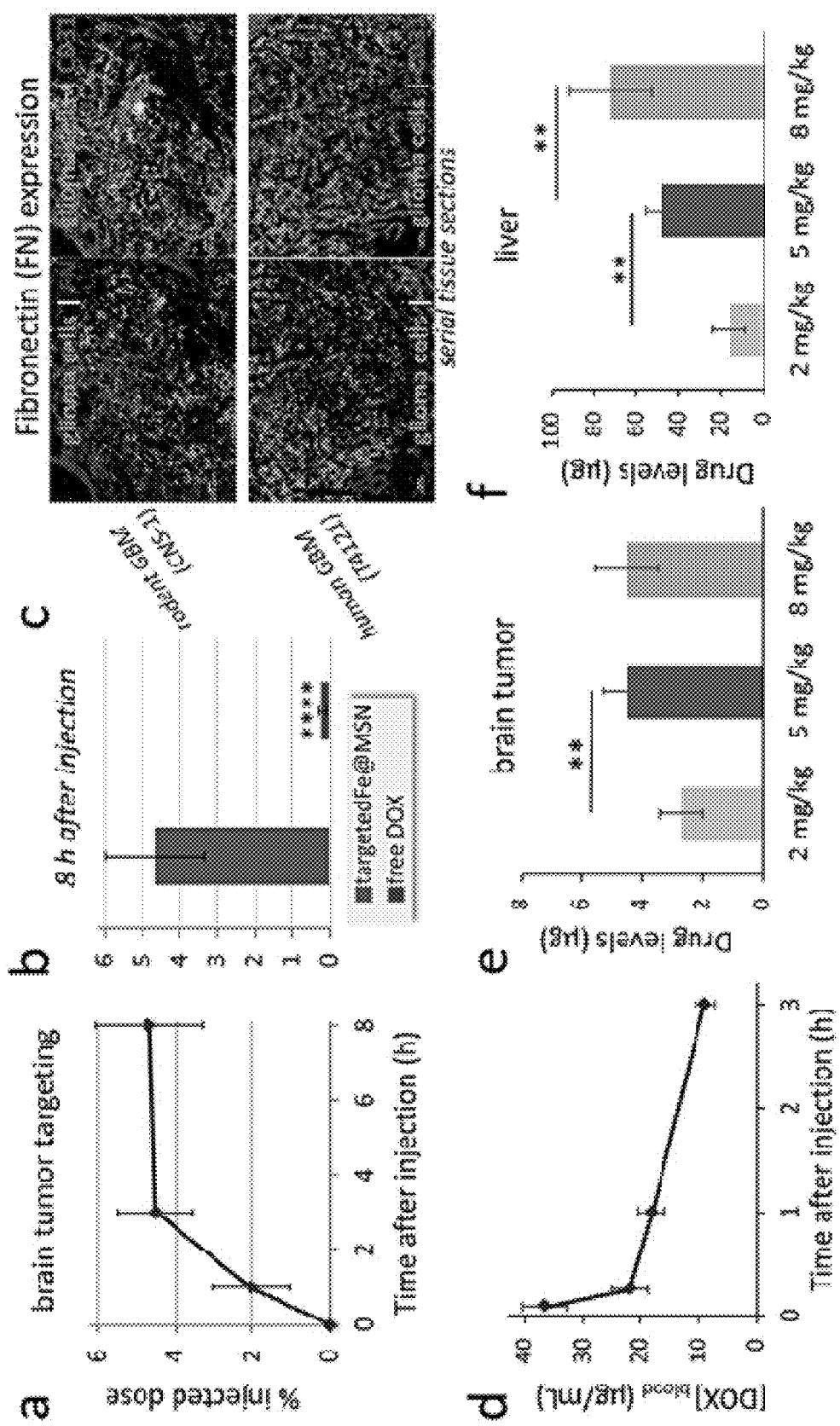
FIGS. 4(A-F) illustrate plots graphs and images showing organ distribution of the Fe@MSN nanoparticles decorated with cRGD peptides in mice bearing orthotopic CNS-1 brain tumors. (A) Organ and tumor distribution 3 h after administration of cRGD-targeted Fe@MSN particles loaded with DOX at a dose of 5 mg DOX per kg b.w. (B) Accumulation of cRGD-targeted Fe@MSN particles in brain tumors 1 and 3 h after systemic administration of the particles (n=5 per group.). (C) Histological analysis of the degree and topology of fibronectin in two glioma models in mice (T4121 & CNS-1 models; 20× magnification; green: glioma cells; red: fibronectin; purple: endothelial cells). (D) Pharmacokinetic profile of the MSN particles (n=5). Biodistribution of the MSN nanoparticles 24 h after IV injection in the (E) liver and (F) spleen at three different doses.

The organ distribution of the integrin-targeting cRGD-Fe@MSN nanoparticles was evaluated in the CNS-1 rodent glioma model at 1 and 3 h after tail vein administration (n=5 mice per group). After animals were euthanized at the designated time point after injection, organs were perfused, excised, homogenized and the levels of drugs were directly measured in tissues using HPLC. At 3 h after injection, the majority of the particles were cleared by the liver, while the levels of nanochains in the heart, lungs, and kidney were very low (FIG. 4A). Most importantly, vascular targeting of MPNC resulted in significant drug deposition in the brains of the glioma-bearing animals compared to negligible amounts in healthy brains. More specifically, the particles started depositing to glioma sites rapidly. Within 1 h after injection, 2% of the injected dose accumulated in the brain tumors, whereas the particles deposition in glioma sites plateaued within 3 h to the remarkable 4.5% of the dose (FIG. 4B).

Evaluation of RF-Triggered Drug Release In Vivo

Figure 5:
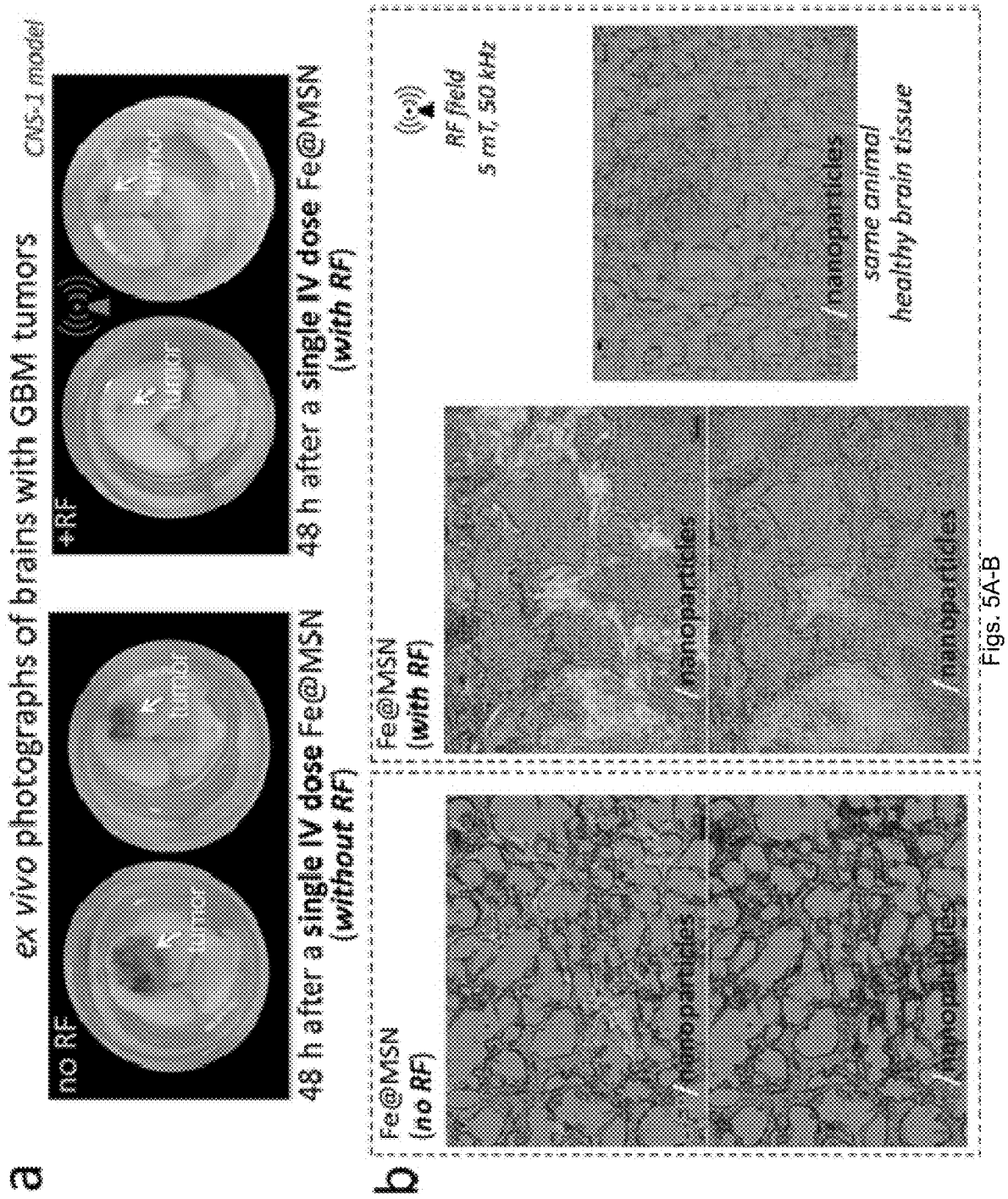
FIGS. 5(A-B) illustrate images showing the evaluation of the anticancer effect of RF-triggered drug release from the Fe@MSN nanoparticles in vivo. (A) Using the orthotopic CNS-1 model in mice, photographs of brains show the treatment response of the RF-triggered release of DOX in animals treated with Fe@MSN. All animals were euthanized 48 h after a single dose of DOX-loaded Fe@MSN particles at a low dose (2 mg/kg). (B) Histological analysis was performed 48 h after the animals were treated with a single dose of DOX-loaded Fe@MSN particles. Using the fluorescence properties of DOX, fluorescence microscopy shows the widespread distribution of DOX molecules (purple: DOX) after a 60-min application of RF (10× magnification). The distribution of DOX molecules is shown with (left panel) or without RF (right panel). Fe@MSN particles were visualized by staining iron with Prussian blue.

While no widespread delivery of drugs was observed in the case of Fe@MSN-treated animals that were not exposed to RF, application of the RF field facilitated the spread of drug across the BTB barrier with significant anticancer outcomes (FIG. 5A). In some instances, we used doxorubicin as a model drug because of its high cytotoxicity and mild fluorescence, which allowed visualisation of drug delivery in histology. We histologically determined that 1) Fe@MSN nanoparticles localized at the brain-tumor interface in primary and invasive GBM sites, 2) the degree and topology of drug delivery after the application of RF, and 3) the anticancer effect of the released drugs to different cell subpopulations of the glioma tumors as evaluated by the TUNEL assay (FIG. 5B).

Evaluation of Therapeutic Efficacy In Vivo

Figure 6:
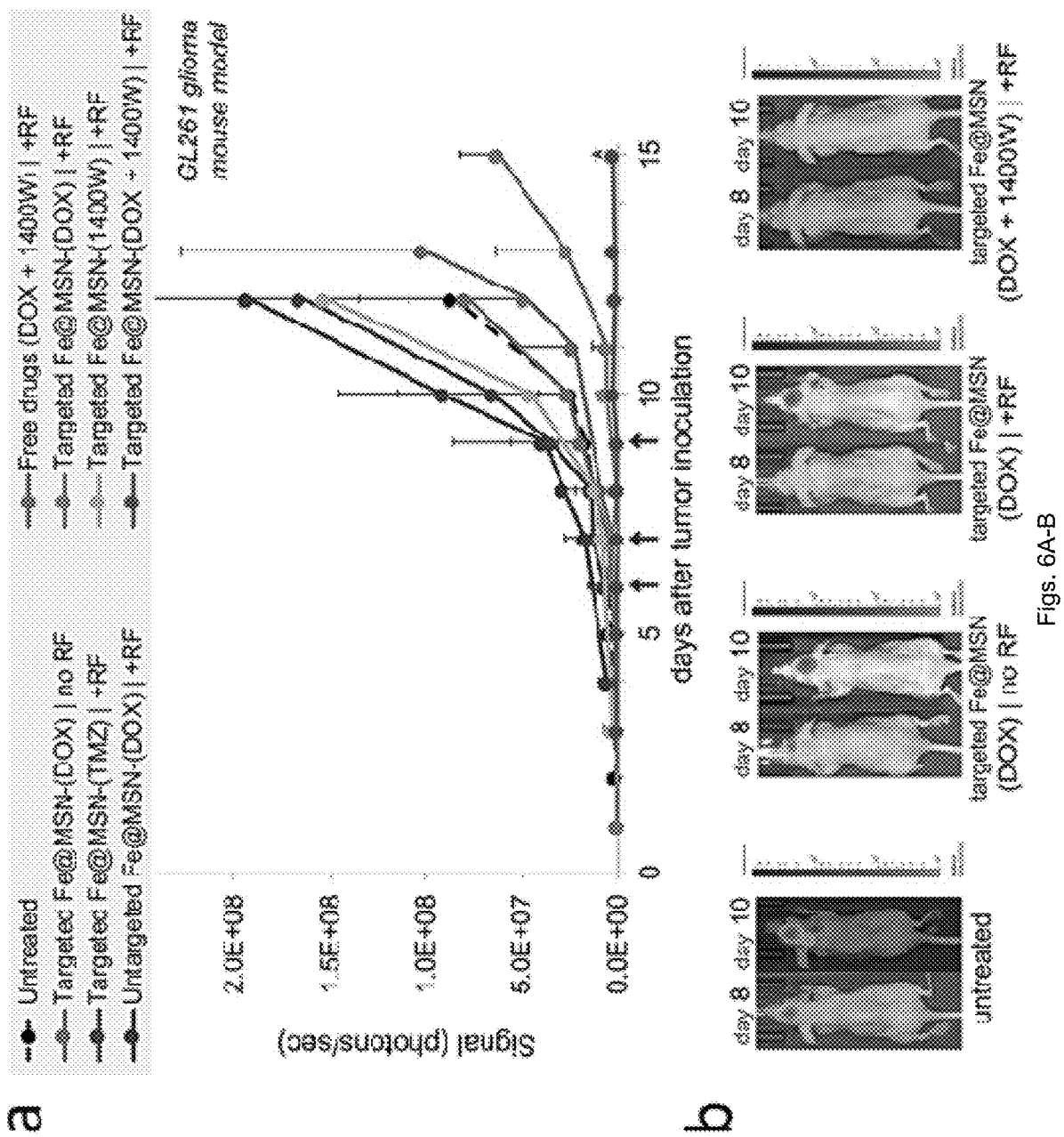
FIGS. 6(A-B) illustrate a plot and images showing evaluation of therapeutic efficacy of Fe@MSN treatments in vivo. (A) Various formulations were i.v. injected in mice bearing orthotopic GL261 brain tumor on day 6, 7 and 9 after tumor inoculation. Treatments included free drugs, DOX-loaded Fe@MSN (5 mg/kg) or a cocktail containing DOX-loaded Fe@MSN (5 mg/kg) and 1400 W-loaded Fe@MSN (10 mg/kg). In the case of treatments combined with the RF field, animals were exposed for 60 min to the RF field (5 mT, 50 kHz). The response to treatment was monitored using longitudinal bioluminescence imaging (BLI). Quantification of the whole head BLI light emission is shown for the (n=7 mice in each group; unpaired t-test P=0.028). (B) Representative BLI images are shown.

We tested the in vivo therapeutic efficacy of Fe@MSN loaded with DOX or 1400 W in the orthotopic GL261 model in mice. The GL261 cells stably expressed firefly luciferase, which allowed in vivo bioluminescence Imaging (BLI). Using BLI signal as a measure of short-term tumor response to various treatments, we compared free DOX and 1400 W to Fe@MSN loaded with DOX or 1400 W. Considering the short lifespan of GBM models in mice, we employed a treatment protocol with a realistic schedule and dosages. Animals were treated three times with free drugs or drug-loaded Fe@MSN formulations (with or without RF) on day 6, 7 and 9 after tumor inoculation. Drugs were systemically administered at a dose of 8 mg doxorubicin and 10 mg 1400 W per kg of body weight. After the last treatment on day 9, we monitored the response of the tumor to various drugs and formulations. As a metric of the response to various treatments, quantification of BLI signal was used (FIG. 6A). Representative BLI images are shown in FIG. 6B. The treatment with free drugs had negligible therapeutic benefits, while the DOX-loaded Fe@MSN treatment (without RF) also exhibited an insignificant effect. The application of RF on animals treated with DOX-Fe@MSN exhibited an improved outcome. However, the application of RF on animals that were treated with the cocktail of DOX-loaded Fe@MSN and 1400 W-loaded Fe@MSN resulted in a significant anticancer outcome.

Since the treatment with the anti-BTIC inhibitor 1400 W exhibited significant benefits, we examined the topology of the nanoparticle deposition by performing immunohistochemistry in a small subset of the animals (n=3). The CREKA-targeted nanoparticles displayed a perivascular deposition across the brain tumor. Most importantly, the nanoparticles exhibited equally significant deposition in hypoxic regions that often contain highly resistant subpopulations of glioma cells. These were exactly the regions that were enriched in BTICs expressing stem cell markers (OLIG2 and SOX2).

For survival studies, we used the 9 L glioma model in mice. We used standard chemotherapy (TMZ, DOX) and 1400 W (iNOS inhibitor that kills stem cells in their standard free form or loaded into the Fe@MSN nanoparticles.

Figure 7:
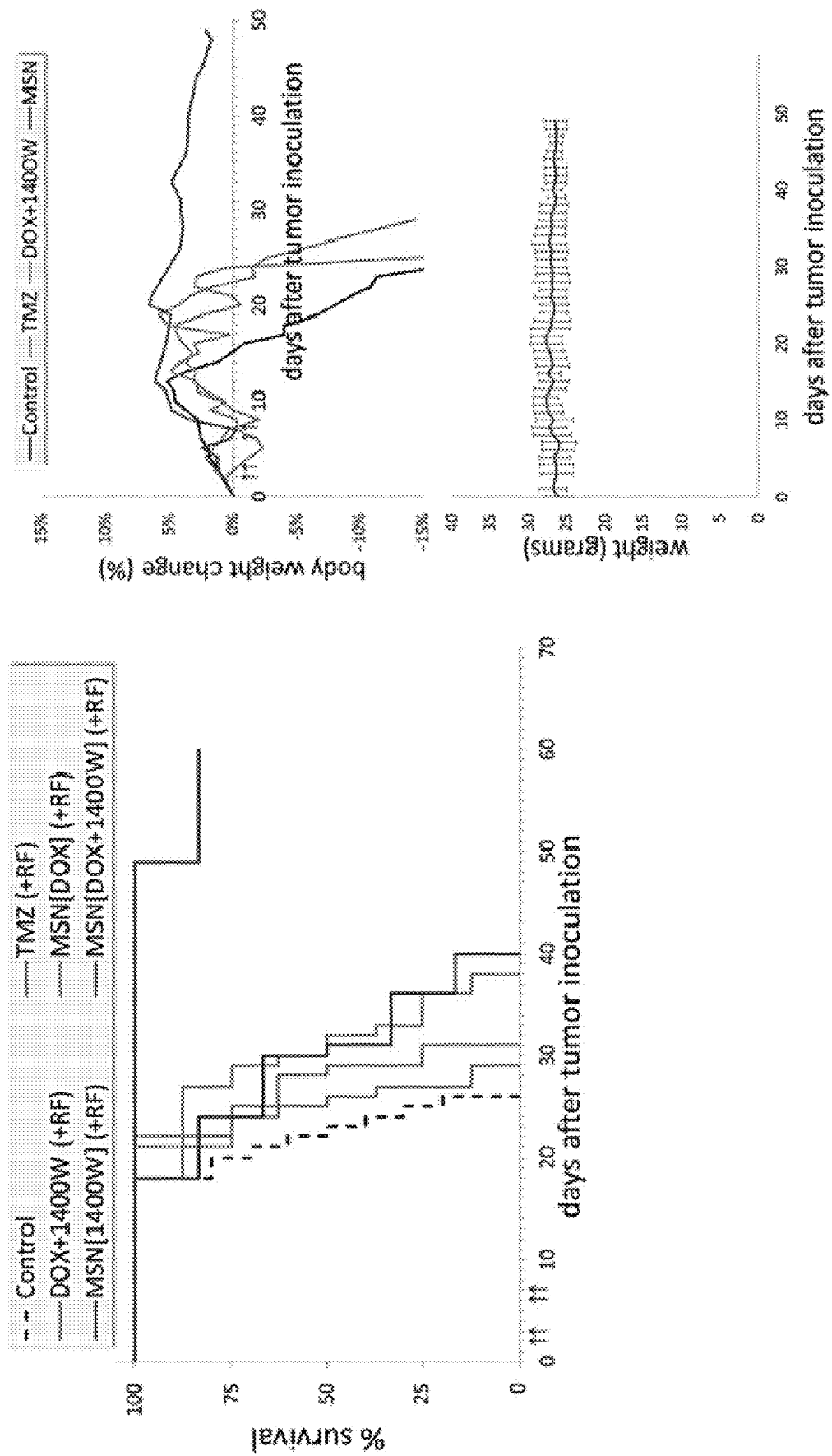
FIG. 7 illustrates survival curves. In the orthotopic 9 L glioma model in mice, the survival time of animals treated with DOX-loaded nanoparticles and 1400 W-loaded nanoparticles (+RF) is compared to that of animals treated with free drugs (TMZ, 1400 W+DOX; +RF) and the untreated group (n=8 mice in each group). Each formulation was administered at a dose of 5 mg DOX and 10 mg 1400 W per kg of body weight. Treatments were systemically administered via a tail vein injection four times at days 2, 3, 6 and 7 after tumor inoculation (blue arrows). Statistical significance was determined using the log-rank (Mantel-Cox) test (P<0.0001). The body weight of all the animals was monitored on a daily basis.

In addition to the survival curves (FIG. 7), we also show the body weights of the animals as a metric of response to the various treatments as well as the disease burden.

Figure 8:
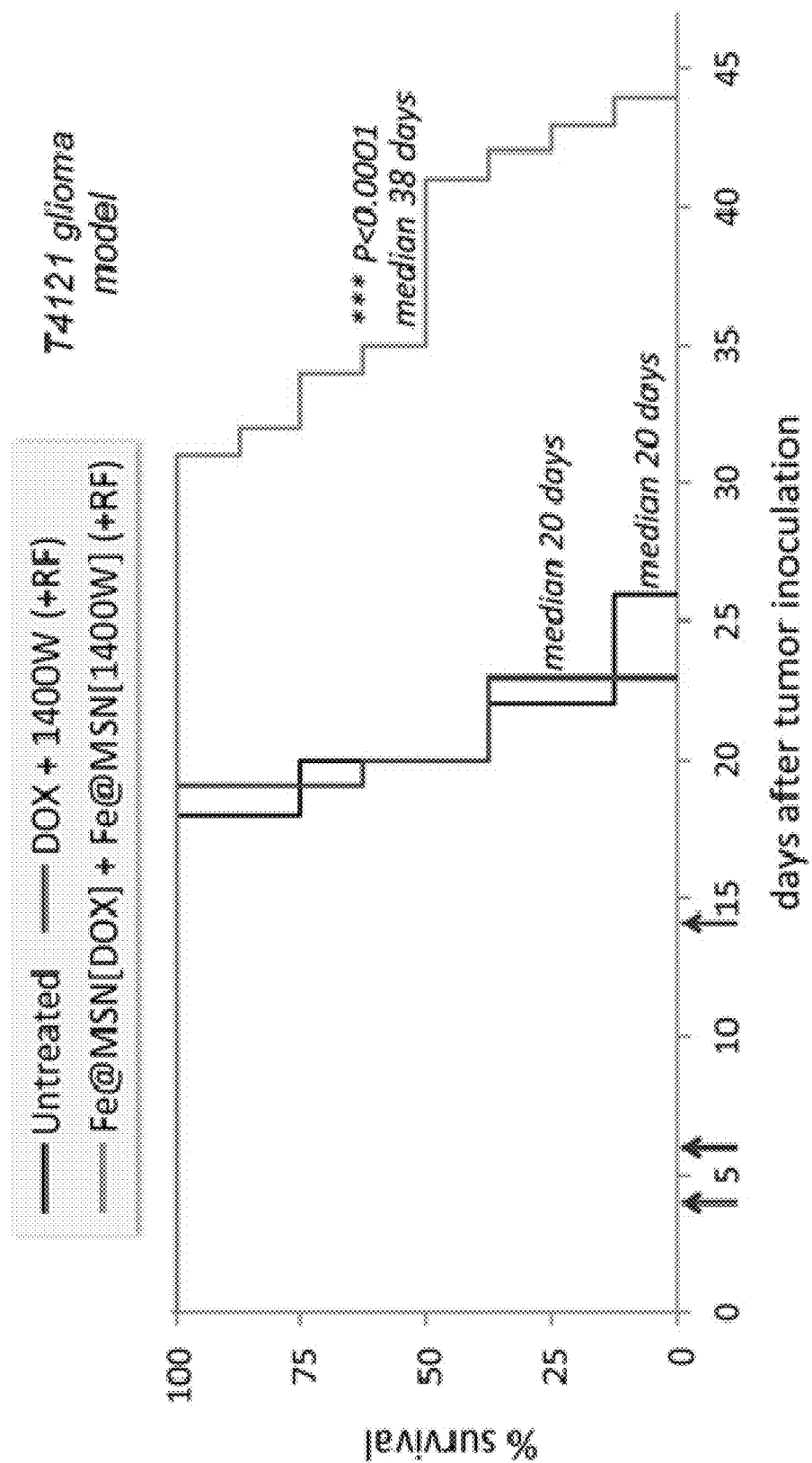
FIG. 8 illustrates survival curves. In the orthotopic T4121 glioma model in mice, the survival time of animals treated with DOX-loaded nanoparticles and 1400 W-loaded nanoparticles (+RF) is compared to that of animals treated with free drugs (1400 W+DOX; +RF) and the untreated group (n=8 mice in each group). Each formulation was administered at a dose of 5 mg DOX and 10 mg 1400 W per kg of body weight. Treatments were systemically administered via a tail vein injection three times at day 4, 6, and 14 after tumor inoculation (blue arrows). Statistical significance was determined using the log-rank (Mantel-Cox) test (P<0.0001).
Figure 9A:
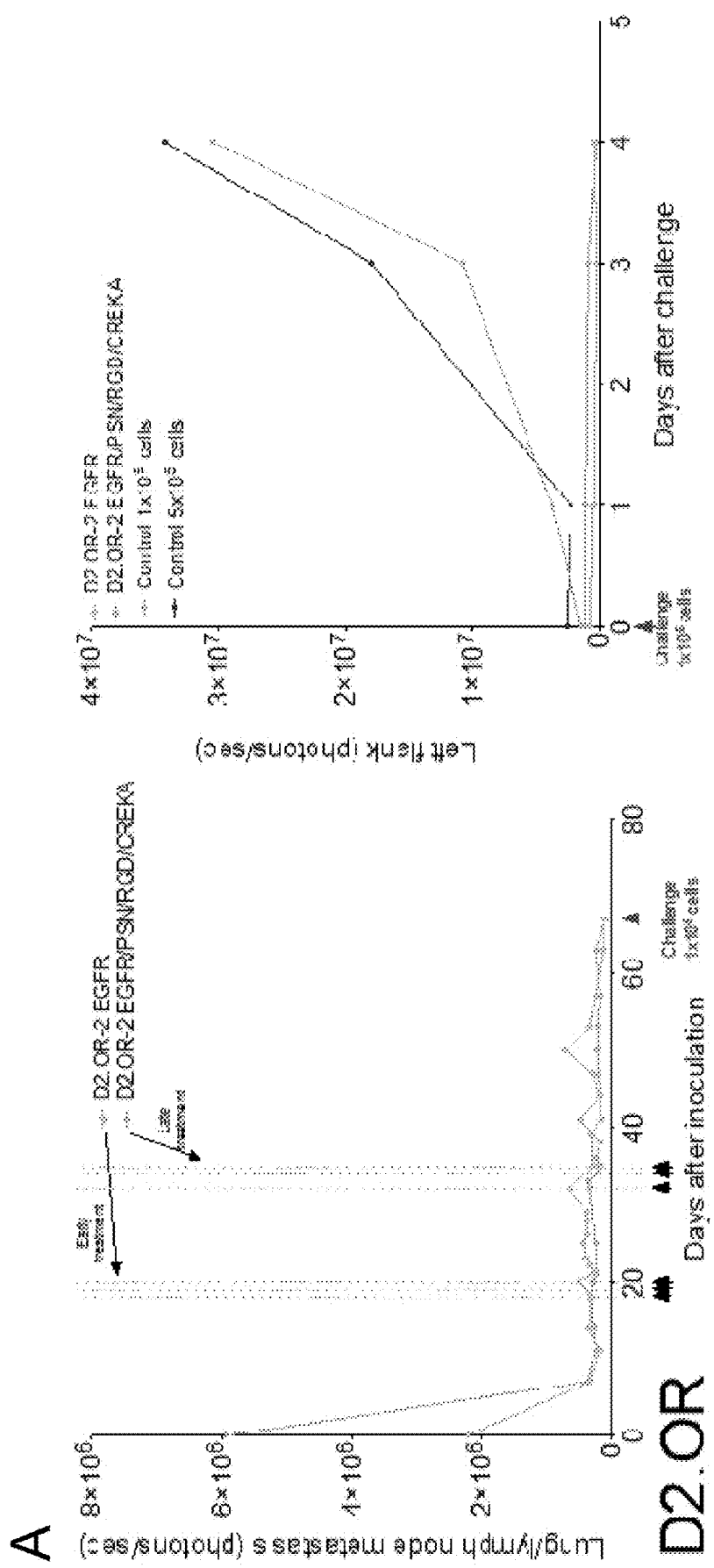
FIGS. 9(A-B) illustrate plots showing immunotherapy data.
Figure 9B:
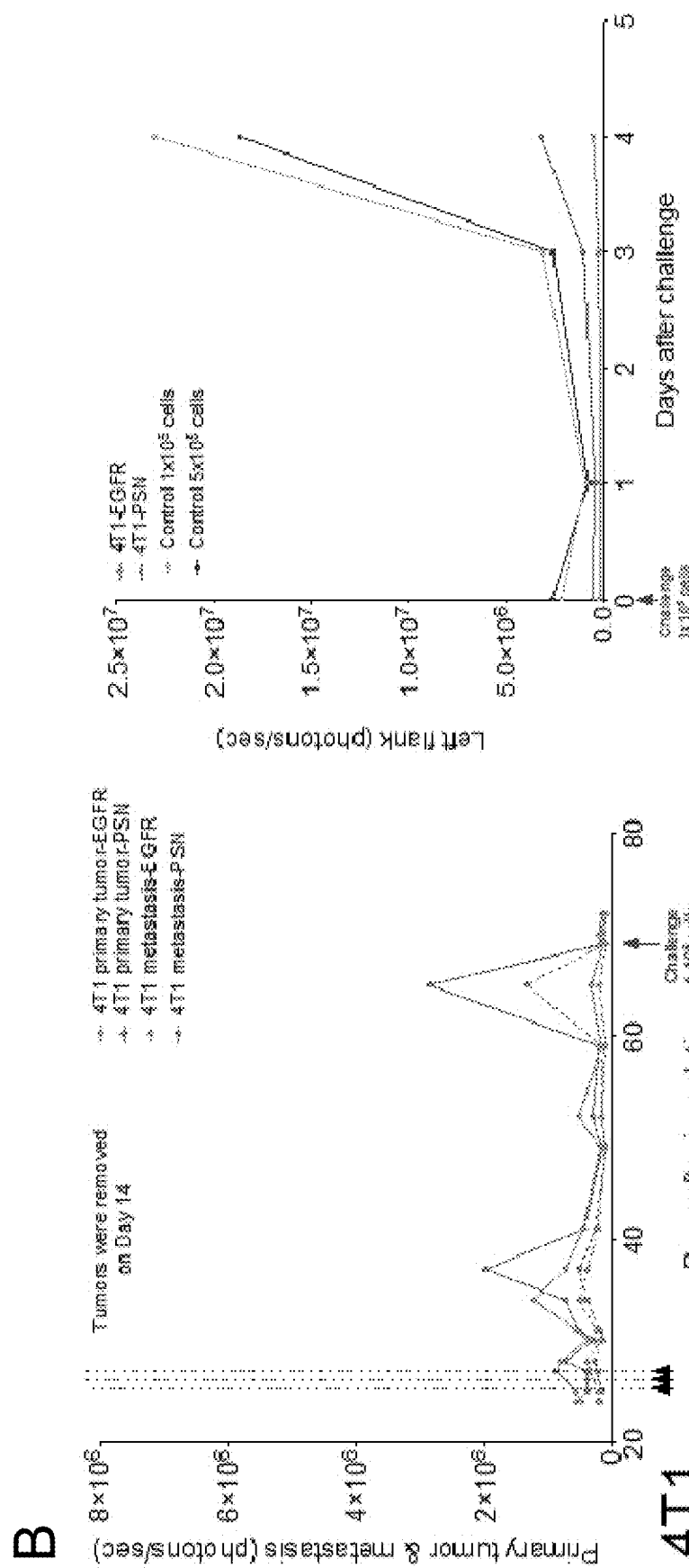

We also selected a xenograft model based on human glioma cells containing brain tumor initiating cells (BTICs), which exhibit increased resistance to radiation and chemotherapy. GBMs display remarkable cellular hierarchies with tumorigenic brain tumor initiating cells (BTICs) at the apex. The glioma xenograft was based on GBM tissue obtained from excess surgical materials of a recurrent GBM (specimen T4121). In particular, the T4121 glioma cells contain BTICs with an increased capacity for tumor propagation. To assess the therapeutic efficacy of the Fe@MSN treatment, we measured survival times in the T4121 model in mice (FIG. 8). The control treatment included standard DOX and 1400 W followed by RF. Treatments were administered only three times. In agreement to the studies in the GL261 model, the tumor response to free DOX and 1400 W treatment was negligible as indicated by the survival time being similar to the untreated group (median was 20 days for both groups). Even though the T4121 model exhibits increased chemoresistance, three doses of the Fe@MSN treatment containing DOX and 1400 W (+RF) resulted in a nearly 2-fold increase in survival.

Evaluation of the Therapeutic Efficacy in Survival Studies

We used the T4121 glioma xenograft model, which is based on GBM tissue obtained from excess surgical materials. These glioma cells contain glioma stem cells with an increased capacity for tumor propagation and resistance to chemotherapy and radiation therapy. We used standard chemotherapy (DOX) and 1400 W (iNOS inhibitor that kills stem cells in their standard free form or loaded into the Fe@MSN nanoparticles.

Immunotherapy Applications

Mounting a robust site-specific anti-tumor immune response that harnesses both innate and adaptive immunity can reverse the profound immunosuppression that drives the formation of immune deserts and immune exclusion within the tumor microenvironment (TME). The TME of these cancers has significant numbers of infiltrating pro-tumor immune cells that, along with tumor and other tumor-associated cells, secrete high levels of immunosuppressive molecules that impair the function of local antigen-presenting cells (APCs) and T cells and enables the tumor to remain immune-excluded and hidden from systemic immuno-surveillance. Notably, using a robust immune-potentiating 'alarm bell' stimulus to drive this anti-tumor immune response from within the TME itself has significant advantages over traditional approaches that target lymph nodes exclusively with the aim of increasing systemic immunity. Cancer vaccine efficacy often falls short for this reason, since efforts to augment systemic immunity are not effective when these immune cells cannot overcome TME immunosuppression to home to tumor sites and maintain their activation and tumors remain immune-excluded. Towards this goal, here we present a nanotechnology approach to 're-engineer' immunity within the TME by selectively delivering two synergistic immune-potentiating agents specifically to the APC-rich perivascular niche of the TME to create an IFNβ-driven 'alarm bell' stimulus to bolster innate immunity and mediate adaptive immunity both locally and systemically. We selected the 4T1 murine model of TNBC as an optimal test-bed for this therapy since it is poorly immunogenic, significantly immunosuppressive, and exhibits spontaneous metastasis.

We harnessed the innate immune pathway to trigger a potent immune response by using the Fe@MSN particles to deliver a strong inducer of Type I interferons, the Stimulator of Interferon Genes (STING) agonist cyclic diguanylate monophosphate (cdGMP), which has gained significant attention in recent years. STING agonists are used as vaccine adjuvants and target host pattern recognition receptors (PRRs), which recognize conserved, immunogenic molecules from viruses and bacteria (i.e., specific nucleic acids, cell membrane components) and trigger the appropriate immune response. STING agonists are cyclic dinucleotides and small-molecule second messengers that, when free in the cytosol, bind STING machinery to trigger the robust production of Type I interferons. The Fe@MSN particles were synthesized using the method described previously. Instead of phosphonate, we used functionalization with APTES as an internal coating of the silica pores, which enhanced loading of cdGMP into the nanoparticle (140 μg per mg of nanoparticles).

Models of metastatic breast cancer were developed by inoculating BalbC mice with just 5×10$^5$ cells/50 μL via tail vein injection. Doses were 20 μg CDN per animal. RF treatment was performed 3 h after injection. Treatment groups included (1) D2.OR and D2.A1 treated when A1 tumor signal increased significantly (days 18, 19, and 20). Treated with EGFR-targeted MSNs. (2) D2.OR treated later when some OR signal increased significantly (days 32, 34, and 35). Treated with a cocktail of equivalent amounts of EGFR-/PSN-/RGD-/CREKA-targeted MSNs. FIG. 8 indicates that the treatment successfully generated immunological memory.

From the above description of the application, those skilled in the art will perceive improvements, changes and modifications. Such improvements, changes, and modifications are within the skill of those in the art and are intended to be covered by the appended claims. All patents, patent applications, and publication cited herein are incorporated by reference in their entirety.

Having described the invention, we claim:

1. A system for delivering a therapeutic agent to cell or tissue of a subject, the system comprising:
    a nanoparticle that includes an iron oxide core, a layer of mesoporous silica coated over and contiguous with the iron oxide core, and one or more therapeutic agents that are entirely contained in the mesoporous silica layer of the nanoparticle; and
    a remote radiofrequency (RF) energy source for applying RF energy to the nanoparticle effective to release the one or more therapeutic agents from the mesoporous silica layer of the nanoparticle by mechanical tumbling and/or vibration of the nanoparticle, wherein release of the one or more therapeutic agents not caused by a hyperthermic response of the nanoparticle to the RF energy.

2. The system of claim 1, the nanoparticle further comprising at least one targeting moiety.

3. The system of claim 2, wherein the at least one targeting moiety is linked to the exterior surface of the mesoporous silica layer of the nanoparticle.

4. The system of claim 3, including multiple targeting moieties, wherein the spacing and location of the targeting moieties on each nanoparticle is controlled to facilitate delivery, targeting, and/or therapeutic efficacy of the nanoparticle when administered to the subject.

5. The system of claim 1, the nanoparticle having a diameter of about 50 nm to about 150 nm.

6. The system of claim 1, the iron oxide core having a diameter of about 10 nm to about 50 nm.

7. The system of claim 1, the therapeutic agent comprising an anti-cancer agent.

8. The system of claim 1, the remote energy source being external to the subject.

9. The system of claim 1, the RF energy effective to release the one or more therapeutic agents being less than that required to induce a localized temperature increase in the subject.

10. The system of claim 1, wherein the RF energy is supplied at a frequency of about 1 kHz to about 50 kHz.

11. The system of claim 1, further comprising one or more imaging agents contained in, and/or conjugated to the mesoporous silica layer of the nanoparticle.

12. The system of claim 1, the one or more therapeutic agents comprising one or more anti-cancer agents.

13. The system of claim 11, the nanoparticles being provided in a composition effective for intravenous delivery to the subject.

14. A method of treating cancer in a subject, the method comprising:
    administering to the subject a plurality of nanoparticles, each nanoparticle including an iron oxide core, a layer of mesoporous silica coated over and contiguous with the iron oxide core, and one or more anti-cancer agents that are entirely contained in the mesoporous silica layer of the nanoparticle,
    applying radiofrequency (RF) energy from a remote source external to the subject to the nanoparticles effective to release the one or more therapeutic agents from the mesoporous silica layer of the nanoparticles by mechanical tumbling and/or vibration of the nanoparticles, wherein release of the one or more therapeutic agents not caused by a hyperthermic response of the nanoparticles to the RF energy.

15. The method of claim 14, the nanoparticle having a diameter of about 50 nm to about 150 nm and the iron oxide core having a diameter of about 10 nm to about 50 nm.

16. The method of claim 14, the nanoparticle further comprising at least one targeting moiety that is linked to the exterior surface of the mesoporous silica layer of the nanoparticle.

17. The method of claim 14, the nanoparticles being delivered intravenously to the subject and applying RF energy from the remote RF energy source to the administered nanoparticles localized to cancer cells of the cancer to release the one or more anti-cancer agents from the mesoporous silica layer of the nanoparticle.

18. The method of claim 14, the RF energy effective to release the one or more anti-cancer agents being less than that required to induce a localized temperature increase in the subject.

19. The method of claim 14, wherein the RF energy is applied at about 1 kHz to about 50 kHz.

20. The method of claim 14, the one or more anti-cancer agents comprising one or more chemotherapeutic agents.

\* \* \* \* \*